United States Patent
Zheng et al.

(10) Patent No.: US 7,115,383 B2
(45) Date of Patent: Oct. 3, 2006

(54) ASSAYS FOR AMPHETAMINE AND METHAMPHETAMINE

(75) Inventors: Yi Feng Zheng, Wilmington, DE (US); Richard F. Parrish, San Jose, CA (US); Johnny Valdez, Fremont, CA (US); Hshiou-ting Liu, Milpitas, CA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 10/806,327

(22) Filed: Mar. 22, 2004

(65) Prior Publication Data

US 2005/0208604 A1    Sep. 22, 2005

(51) Int. Cl.
- G01N 33/535 (2006.01)
- G01N 33/531 (2006.01)
- C07K 16/00 (2006.01)
- C07K 17/02 (2006.01)

(52) U.S. Cl. ............ 435/7.9; 435/961; 435/975; 435/7.1; 435/188; 436/544; 436/546; 530/388.9; 530/389.8; 530/402; 530/405

(58) Field of Classification Search ........... 564/336; 436/7.1, 544, 546; 530/388.9, 389.8, 409, 530/402, 403, 405; 435/188, 961, 7.9, 7.1, 435/975

See application file for complete search history.

(56) References Cited

U.S. PATENT DOCUMENTS

| | | | |
|---|---|---|---|
| 1,879,003 A | 9/1932 | Alles | 564/381 |
| 1,921,424 A | 8/1933 | Nabenhauer | 167/58 |
| 2,344,356 A | 3/1944 | Hildebrandt | 260/570.8 |
| 3,117,160 A | 1/1964 | Holland | 260/570.8 |
| 3,547,999 A | 12/1970 | Shulgin | 260/570.8 |
| 3,709,868 A | 1/1973 | Spector | 260/121 |
| 3,758,691 A | 9/1973 | Carlsson et al. | 424/330 |
| 3,763,218 A | 10/1973 | Kaiser et al. | 260/471 A |
| 3,766,162 A | 10/1973 | Spector | 260/112 R |
| 3,775,536 A | 11/1973 | Spector et al. | 424/1 |
| 3,847,950 A | 11/1974 | Suh et al. | 260/340.5 |
| 3,867,366 A | 2/1975 | Rubenstein et al. | 260/121 |
| 3,875,011 A | 4/1975 | Rubenstein et al. | 195/99 |
| 3,911,016 A | 10/1975 | Klingler et al. | 260/570.8 R |
| 3,995,021 A | 11/1976 | Gross | 424/1.5 |
| 3,996,344 A | 12/1976 | Gross | 424/1.5 |
| 4,016,146 A | 4/1977 | Soares | 260/112 R |
| 4,022,878 A | 5/1977 | Gross | 424/1.5 |
| 4,036,823 A | 7/1977 | Soares | 260/112 R |
| 4,041,076 A | 8/1977 | Avenia et al. | 260/559 A |
| 4,058,642 A | 11/1977 | Renth et al. | 424/330 |
| 4,064,228 A | 12/1977 | Gross | 424/1 |
| 4,073,798 A | 2/1978 | Suh | 260/340.5 R |
| 4,097,586 A | 6/1978 | Gross | 424/1 |
| 4,129,598 A | 12/1978 | Giudicelli et al. | 260/570.8 R |
| 4,218,539 A | 8/1980 | Weltman | 435/188 |
| 4,220,565 A | 9/1980 | Katz | 260/6 |
| 4,329,281 A | 5/1982 | Christenson et al. | 260/112 B |
| 4,595,656 A | 6/1986 | Allen et al. | 435/7 |
| 4,680,338 A | 7/1987 | Sundoro | 525/54.1 |
| 4,686,181 A | 8/1987 | Dona | 435/7 |
| 4,760,142 A | 7/1988 | Primes et al. | 544/287 |
| 4,843,147 A | 6/1989 | Levy et al. | 530/391 |
| 4,847,195 A | 7/1989 | Khanna et al. | 435/7 |
| 4,868,132 A | 9/1989 | Byrnes et al. | 436/546 |
| 4,952,336 A | 8/1990 | Byrnes et al. | 252/301.16 |
| 4,990,443 A | 2/1991 | Huber et al. | 435/7.9 |
| 5,026,827 A | 6/1991 | Miyazaki et al. | 530/405 |
| 5,101,015 A | 3/1992 | Byrnes et al. | 530/363 |
| 5,135,863 A | 8/1992 | Hu et al. | 435/188 |
| 5,145,791 A | 9/1992 | Zeitvogel et al. | 436/546 |
| 5,198,587 A | 3/1993 | Imai et al. | 564/374 |
| 5,227,472 A | 7/1993 | Yoshioka | 530/403 |
| 5,233,025 A | 8/1993 | Miyazaki et al. | 530/388.9 |
| 5,256,409 A | 10/1993 | Blincko | 424/85.8 |
| 5,262,333 A | 11/1993 | Heiman et al. | 436/537 |
| 5,266,720 A | 11/1993 | Gallacher et al. | 560/60 |
| 5,270,166 A | 12/1993 | Parsons et al. | 435/7.4 |
| 5,294,638 A | 3/1994 | Hell et al. | 514/452 |
| 5,328,828 A | 7/1994 | Hu et al. | 435/7.9 |
| 5,336,621 A | 8/1994 | Primes et al. | 436/534 |
| 5,354,693 A | 10/1994 | Brynes et al. | 436/537 |
| 5,372,949 A | 12/1994 | Zeitvogel et al. | 436/546 |
| 5,373,092 A | 12/1994 | Gallacher et al. | 435/7.93 |
| 5,424,204 A | 6/1995 | Aoyama et al. | 435/188 |
| 5,470,997 A | 11/1995 | Buechler et al. | 558/254 |
| 5,492,841 A | 2/1996 | Craig | 436/534 |
| 5,501,987 A | 3/1996 | Ordonez et al. | 436/534 |
| 5,514,559 A | 5/1996 | Markert-Hahn et al. | 435/7.92 |
| 5,518,887 A | 5/1996 | Parsons et al. | 435/7.1 |

(Continued)

FOREIGN PATENT DOCUMENTS

DE    2844427    4/1980

(Continued)

Primary Examiner—Mary E. Ceperley
Assistant Examiner—Shafiqul Haq
(74) Attorney, Agent, or Firm—Theodore J. Leitereg

(57) ABSTRACT

Methods, compositions and kits are disclosed. The compounds disclosed comprise an amphetamine moiety and a methamphetamine moiety linked together by a first linking group. A second linking group depends from the first linking group and comprises a functional group. The distance of the amphetamine moiety and the methamphetamine moiety from the point of linkage of the second linking group to the first linking group is approximately the same. The compounds may be linked to labels and used in assays for the detection of amphetamine and/or methamphetamine in samples suspected of containing these drugs.

44 Claims, 8 Drawing Sheets

U.S. PATENT DOCUMENTS

| | | | |
|---|---|---|---|
| 5,525,524 A | 6/1996 | Buechler et al. | 436/518 |
| 5,610,283 A | 3/1997 | Buechler | 530/404 |
| 5,616,503 A | 4/1997 | Self | 436/518 |
| 5,643,732 A | 7/1997 | Strahilevitz | 435/7.1 |
| 5,840,588 A | 11/1998 | Strahilevitz | 436/518 |
| 5,851,776 A | 12/1998 | Valkirs | 435/7.1 |
| 5,976,812 A | 11/1999 | Huber et al. | 435/7.1 |
| 6,033,890 A | 3/2000 | Jakobovits et al. | 435/190 |
| 6,090,567 A | 7/2000 | Jakobovits et al. | 435/7.9 |
| 6,140,137 A | 10/2000 | Sigler et al. | 436/536 |
| 6,214,859 B1 | 4/2001 | Yoneda et al. | 514/419 |
| 2003/0170917 A1 | 9/2003 | Hui et al. | 436/547 |
| 2003/0175995 A1 | 9/2003 | Hui | 436/547 |

FOREIGN PATENT DOCUMENTS

| | | | |
|---|---|---|---|
| EP | 0 183901 A2 | 11/1985 | 33/531 |
| EP | 0 517325 A2 | 6/1992 | 33/532 |
| EP | 1 321772 A1 | 6/2003 | 33/94 |
| GB | 828880 | 2/1960 | |
| GB | 1467560 | 3/1977 | 317/58 |
| JP | 53066417 A | 6/1978 | 436/534 |
| JP | 56125666 A | 10/1981 | 436/537 |
| JP | 63220932 | 9/1988 | 530/388.9 |
| JP | 2069196 A | 3/1990 | |
| WO | WO 86/05189 | 9/1986 | 33/531 |
| WO | WO 90/15798 | 12/1990 | |

ASSAYS FOR AMPHETAMINE AND METHAMPHETAMINE

BACKGROUND OF THE INVENTION

This invention relates to methods, compositions and kits for detecting the presence and/or amounts of amphetamine and/or methamphetamine in samples suspected of containing the same. In particular, the invention relates to bivalent hapten conjugates comprising an amphetamine moiety and a methamphetamine moiety. The conjugate may be employed in assays for amphetamine and/or methamphetamine.

The clinical diagnostic field has seen a broad expansion in recent years, both as to the variety of materials of interest that may be readily and accurately determined, as well as the methods for the determination. Over the last decade, testing for drugs of abuse has become commonplace. This testing is not only for the monitoring of criminal offenders and drug addicts, but employers also use it for the screening of workers. In recent years, immunoassays based on the reaction of an antibody with an antigen have been extensively investigated for this purpose.

Typically, immunoassays employ an antibody whose structure recognizes an analyte in a specific manner. The immunoassay is conducted with a signal producing system that produces a detectible change in signal upon binding of the analyte to the antibody. Accordingly, when testing for an analyte in a sample, a detectible change in signal from that produced with a negative sample of a calibrator is taken as a positive result for the presence of that analyte in the sample.

Amphetamine and methamphetamine stimulate the central nervous system and have been used medicinally to treat hypotension, narcolepsy and obesity. Because of their stimulating effects, the drugs and derivatives have been abused. As a result, assays for the detection of amphetamine and/or methamphetamine in samples are of interest.

There is a problem when the aforementioned assay techniques are employed to assay for amphetamines in a sample suspected of containing amphetamine and/or methamphetamine. The problem arises because these assays employ a single antiserum or antibody that can recognize both amphetamine and methamphetamine. In order for this antibody to recognize both amphetamine and methamphetamine, it is necessary for it to be capable of recognizing a particular spatial and polar organization common to amphetamine and methamphetamine and to lack specific recognition of those structural features of amphetamine and methamphetamine that are different. Because such an antibody recognizes structural features that are common to both of these compounds but lacks specific recognition of the structural features that are different, it is able to recognize both compounds and the assay will produce a positive result for a sample containing amphetamine and/or methamphetamine. However, antibodies that recognize both compounds have been found to recognize molecules other than amphetamine and methamphetamine that share some but not all of the common spatial and polar features of amphetamine and methamphetamine.

The above problem was solved in U.S. Pat. Nos. 5,135,863 and 5,328,828 (Hu, et al.), which disclose an immunoassay to determine the presence of amphetamines in a sample suspected of containing amphetamine and/or methamphetamine by employing four primary reagents. Two of these reagents are two conjugates, each comprised of a functionally similar label bound to an amphetamine analog and a methamphetamine analog, respectively. The other two reagents are an antibody to amphetamine and an antibody to methamphetamine.

There is, however, a need for assays for the detection of amphetamine and/or methamphetamine where the number of reagents employed is reduced from that mentioned above and the assay maintains the same level of sensitivity, specificity, speed and accuracy as the assay disclosed in U.S. Pat. Nos. 5,135,863 and 5,328,828 utilizing four reagents.

SUMMARY OF THE INVENTION

One embodiment of the present invention is a compound comprising an amphetamine moiety and a methamphetamine moiety linked together by a first linking group. A second linking group depends from the first linking group and comprises a functional group. The distance of the amphetamine moiety and the methamphetamine moiety from the point of linkage of the second linking group to the first linking group is approximately the same.

Another embodiment of the present invention is a compound of the formula:

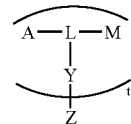

Formula I wherein:
A is an amphetamine moiety,
M is a methamphetamine moiety,
L is a linking group,
Y is a bond, a functional group or a linking group and is bonded to L at a point equidistant between A and M, and
Z is a poly(amino acid), a non-poly(amino acid) label moiety or a functional group;
t is 1 when Z is a functional group or a non-poly(amino acid) label or, when Z is a poly(amino acid), t is an integer between 1 and the molecular weight of a poly(amino acid) divided by about 500;
and salts thereof.

Another embodiment of the present invention is a compound of the formula:

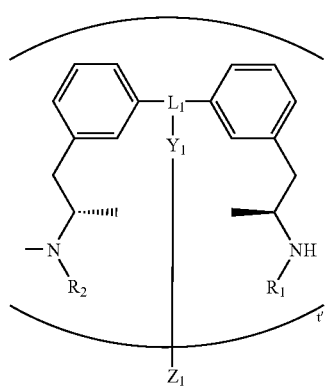

Formula II wherein:

$R_1$ is hydrogen, lower alkyl, or a protecting group, $R_2$ is hydrogen, lower alkyl, or a protecting group, $L_1$ is a linking group, $Y_1$ is a bond, a functional group or a linking group and is bonded to $L_1$ at a point equidistant between the point of attachment to each of the phenyl groups, $Z_1$ is a poly(amino acid), a non-poly(amino acid) label or a functional group; and t' is 1 when $Z_1$ is a functional group or a non-poly(amino acid) label or, when $Z_1$ is a poly(amino acid), t' is an integer between 1 and the molecular weight of a poly(amino acid) divided by about 500;

and salts thereof.

Another embodiment of the present invention is a compound of the formula:

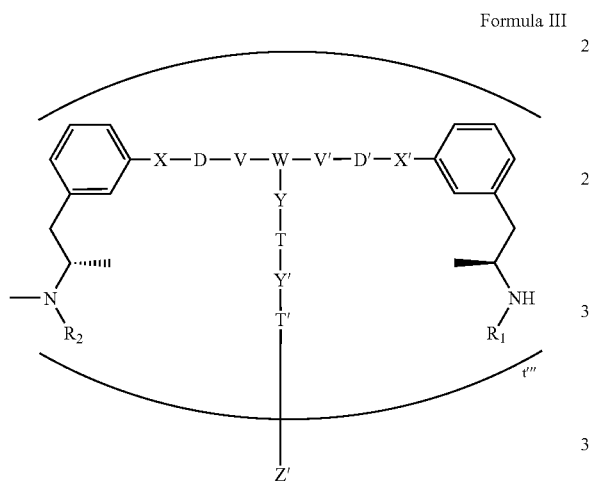

Formula III wherein:

$R_1$ and $R_2$ are independently H, lower alkyl or a protecting group,

X and X' are independently O, S, or a bond;

D and D' are independently alkylene or substituted alkylene;

V and V' are independently O, S, or a bond;

W is CH;

Y is $NR_3$ wherein $R_3$ is H or lower alkyl, O, S, or a bond;

T is alkylene, —(C=O)alkylene, ethereal alkylene, acetamide or a bond;

Y' is $NR_3$ wherein $R_3$ is H or lower alkyl, O, S, or a bond;

T' is alkylene, —(C=O)alkylene, ethereal alkylene, acetamide or a bond; and

Z' is a poly(amino acid), a non-poly(amino acid) label moiety, H, Br, Cl, F, I, $NH_2$, acetamide, haloacetamide;

t'' is 1 when Z' is a functional group or a non-poly(amino acid) label or, when Z' is a poly(amino acid), t'' is an integer between 1 and the molecular weight of a poly(amino acid) divided by about 500;

with the proviso that X and X' have approximately the same length, D and D' have approximately the same length, and V and V' have approximately the same length;

and salts thereof.

Another embodiment of the present invention is a compound of the formula:

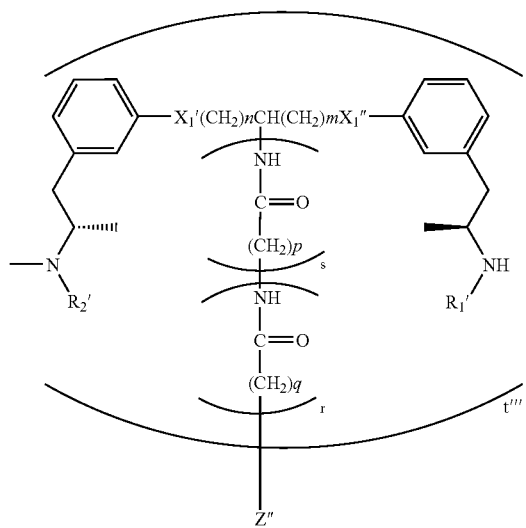

Formula IV wherein:

$R_1'$ and $R_2'$ are independently H, lower alkyl or a protecting group, $X_1'$ and $X_1''$ are S or O;

Z'' is an enzyme; H, Br, Cl, F, I, $NH_2$, acetamide, haloacetamide;

t''' is 1 when Z'' is other than an enzyme and, when Z'' is an enzyme, t''' is an integer between 1 and the molecular weight of the enzyme divided by about 500; and n, m, p, q, r and s are each independently 0 to 5;

and salts thereof.

Another embodiment of the present invention is a compound of the formula:

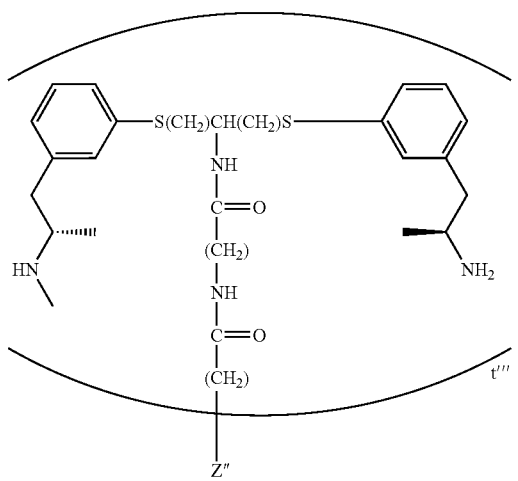

Formula V wherein:

Z'' is an enzyme; and t''' is an integer between 1 and the molecular weight of the enzyme divided by about 500.

Another embodiment of the present invention is a reagent system comprising a compound of Formula I, Formula II, Formula III, Formula IV or Formula V (wherein the compound comprises an enzyme label), an antibody for amphetamine and an antibody for methamphetamine.

Another embodiment of the present invention is a method for determining amphetamine and/or methamphetamine in a sample suspected of containing amphetamine and/or methamphetamine. A combination is provided in a medium where the combination comprises the sample and the aforementioned reagent system. The medium is examined for the presence of a complex comprising the compound of Formula I, Formula II, Formula III, Formula IV or Formula V (wherein the compound comprises an enzyme label) and the antibody for amphetamine and the antibody for methamphetamine. The presence of such complexes indicates the presence of the amphetamine and/or methamphetamine in the sample.

Another embodiment of the present invention is a method for determining amphetamine and/or methamphetamine in a sample suspected of containing amphetamine and/or methamphetamine. A combination is provided in a medium where the combination comprises (i) the sample, (ii) an antibody for amphetamine, (iii) an antibody for methamphetamine, and (iv) a compound of Formula III, which comprises a label. The medium is examined for the presence of a complex comprising the compound of Formula III and the antibody for amphetamine or the antibody for methamphetamine. In one approach, the complex is detected by means of the label. The presence of such complexes indicates the presence of the amphetamine and/or methamphetamine in the sample.

Another embodiment of the present invention is a method for determining amphetamine and/or methamphetamine in a sample suspected of containing amphetamine and/or methamphetamine. A combination is provided in a medium where the combination comprises (i) the sample, (ii) an antibody for amphetamine, (iii) an antibody for methamphetamine, and (iv) a compound of Formula IV, which comprises an enzyme. The medium is examined, usually by determining enzyme activity, for the presence of a complex comprising the compound and the antibody for amphetamine or a complex comprising the compound and the antibody for methamphetamine. The presence of the complexes indicates the presence of the amphetamine and/or methamphetamine in the sample.

Another embodiment of the present invention is a kit comprising in packaged combination (i) an antibody for amphetamine, (ii) an antibody for methamphetamine, and (iii) a compound of Formula I wherein the compound comprises a label.

DESCRIPTION OF THE SPECIFIC EMBODIMENTS

Figure 1:
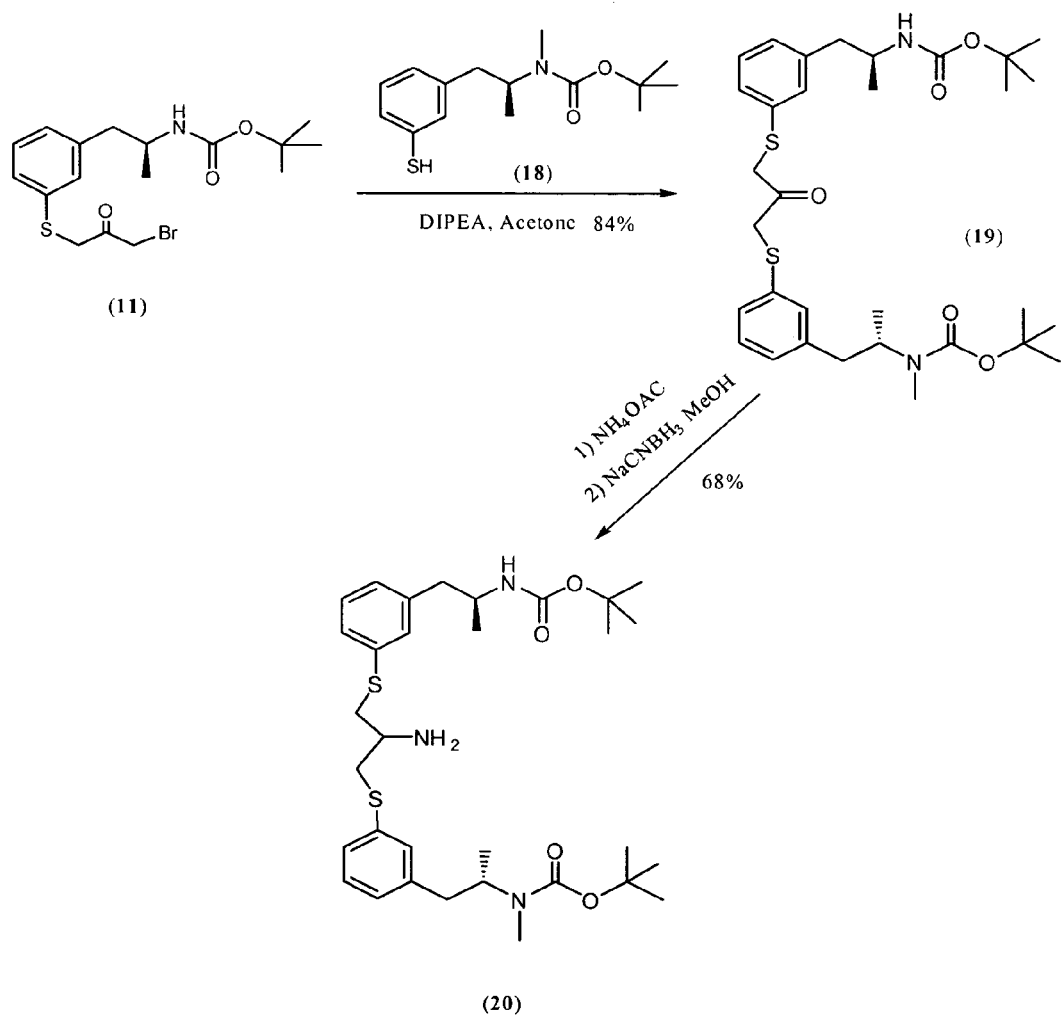
FIG. 1 is a reaction scheme depicting an example of a synthesis of certain compounds in accordance with the present invention.

The present invention permits effective screening of samples for the presence of an amphetamine or a methamphetamine using a smaller number of reagents than that employed in the methods of U.S. Pat. Nos. 5,135,863 and 5,328,828. The methods utilizing the compounds of the invention achieve substantially the same level of sensitivity, specificity, accuracy and speed as the known method.

The assay compositions comprising the compounds of this invention are useful in a wide variety of previously employed assay methods such as, e.g., immunoassay methods, both homogeneous and heterogeneous. The conditions under which these assays have been carried out will normally be applicable to assays employing the present compounds. Thus, the compositions of this invention can be used in prior art immunoassays so as to provide a means to determine the presence of amphetamine and/or methamphetamine in a sample suspected of containing amphetamine and/or methamphetamine. By appropriate choice of components for producing a detectible signal, the detectible signal may be observed visually or by means of various apparatus, i.e., detection means, such as spectrophotometers, fluorometers, scintillation counters, etc.

The assay composition includes the present compounds comprising a label and also includes ancillary reagents necessary to produce a signal from the present compounds. A key reagent in the signal producing system is a single conjugate comprising an amphetamine moiety and a methamphetamine moiety linked together and further linked to a label, either a poly(amino acid) such as an enzyme or a non-poly(amino acid) such as a fluorescent compound. The choice of assay or assay protocol usually determines whether an increase or decrease in the amount of signal generated by the signal producing system determines the amount of amphetamines in the assay sample.

In the present invention, a three-component reagent system that includes a single label conjugate and two antibodies is employed. The present invention utilizes a bivalent hapten reagent that incorporates both amphetamine and methamphetamine moieties in a single chemical entity. This particular synthetic entity can then be conjugated to, for example, a label to produce a label conjugate comprising the amphetamine and methamphetamine moieties. The bivalent haptens comprise a linking group between the two moieties so that both the amphetamine moiety and methamphetamine moiety are extended substantially equally in space and, in some embodiments, are symmetrically disposed, allowing each of the hapten moieties equal opportunity to interact with a corresponding antibody. The linking group typically has a functional group in the middle of its scaffold where the functional group is available for further elaboration of the molecule such as by attaching a linking group for linking to a label. The functional group permits the incorporation of a tether or second linking group, which has a functionality ready for attachment to an attachable moiety, for example, a label such as, e.g., an enzyme. The reagent system further includes two antibodies, namely, an antibody for amphetamine and an antibody for methamphetamine. The reagent system may be used in methods for detecting the aforementioned drugs in samples suspected of containing the drugs. In the assays the amphetamines, i.e., amphetamine and methamphetamine, to be measured are the analytes. In general, an analyte is a ligand and is a member of a specific binding pair, which may be, for example, the ligand or analyte and a corresponding antibody for the ligand or analyte.

Accordingly, one embodiment of the present invention is a compound comprising an amphetamine moiety and a methamphetamine moiety linked together by a first linking group. The amphetamine moiety is generally an analog of amphetamine. A ligand analog such as the amphetamine moiety and the methamphetamine moiety is a modified ligand that, as part of the label conjugate of the invention, can compete with the analogous ligand or analyte for binding to an antibody. The modification of the analog provides means to join a ligand analog to another molecule such as a linking group and ultimately to an attachable moiety such as a poly(amino acid) or a non-poly(amino acid) label. The ligand analog may differ from the ligand by replacement of a hydrogen with a bond which links the ligand analog to the first linking group. The terms "amphetamine moiety" and "methamphetamine moiety" also include derivatives of amphetamine and methamphetamine such as, for example, acids, esters, amides including, e.g., haloacetamide, maleimide and the like.

One set of derivatives involves moieties wherein the amine functionality of the amphetamine or methamphetamine is protected with a protecting group. Suitable types of protecting groups are well known in the art and have been described in detail in numerous patents and articles in the technical literature. See, for example, "Principles of Peptide Synthesis" (M. Bodanszky, Springer Verlag, Berlin, Heidelberg, New York, Tokyo (1984). Such protecting groups include, by way of example and not limitation, t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyl-oxycarbonyl, alpha-dimethyl-3,5-dimethoxybenxyloxycarbonyl, o-nitrophenylsulfenyl, 2-cyano-1,1-dimentyl-ethoxycarbonyl, bromobenzyloxy, carbamyl, formyl, and the like.

In some embodiments, the amphetamine moiety and the methamphetamine moiety are linked to the first linking group in a substantially symmetrical manner. In other words the two moieties are linked to the first linking group from the same corresponding positions in the respective moieties. In this way the moieties are disposed in the bivalent conjugate such that they are essentially mirror images of one another except for the presence of a methyl group in the methamphetamine moiety, instead of hydrogen, on the amine group. In some embodiments, the moieties are linked from the respective phenyl groups and, in some embodiments, from the 3-positions on the respective phenyl groups. However, the moieties may be linked from other positions of the respective molecules and on the phenyl groups as long as the moieties are specifically recognized by their respective antibodies to the extent necessary to obtain a sensitive and accurate assay for amphetamine and/or methamphetamine. For homogeneous assays there should be sufficient competition between the respective antibodies and the amphetamine moiety and methamphetamine moiety of the conjugate on the one hand and the analyte amphetamine and methamphetamine on the other hand to produce a reliable assay. Furthermore, there should be sufficient inhibition of the label such as enzyme label to achieve an accurate and sensitive assay.

In some embodiments, the amphetamine moiety and the methamphetamine moiety are each stereospecific. By this is meant that the amphetamine moiety and the methamphetamine moiety are the respective stereoisomers that are physiologically active.

The first linking group contains a functionality for linking to a second linking group. The amphetamine moiety and the methamphetamine moiety are disposed in the first linking group so that they are substantially equally spaced from the functionality for linking to the second linking group. In some embodiments, the moieties are equally spaced. By "substantially equally spaced" is meant that the spacing need only be sufficient so that the moieties in the subsequent bivalent label conjugate are recognized by their respective antibodies to the extent necessary to produce an accurate and sensitive assay. Thus, in some circumstances the spacing from the functionality for linking to the second linking group may not be equal as long as the above criteria are achieved. In this manner, the distance of the amphetamine moiety and the methamphetamine moiety from the point of linkage of the second linking group to the first linking group is "approximately the same." For the present conjugates the spacing is about 10 Å to about 80 Å, about 10 Å to about 70 Å, about 10 Å to about 60 Å, about 10 Å to about 50 Å, about 10 Å to about 40 Å, about 10 Å to about 30 Å, about 10 Å to about 20 Å, about 12 Å to about 18 Å, about 12 Å to about 16 Å.

The first linking group may comprise about 3 to about 15 atoms, or about 3 to about 10 atoms, not counting hydrogen or the functionality for linking to the second linking group. The first linking group usually comprises a chain of 3, 4, 5, 6, 7, or 8 or more atoms, e.g., from about 3 to about 8 atoms, about 3 to about 7 atoms, about 3 to about 6 atoms, about 4 to about 8 atoms, each independently selected from the group normally consisting of carbon, oxygen, sulfur, nitrogen, halogen and phosphorous, and so forth. The chain comprises a central atom, usually, but not necessarily, a carbon atom, to which the functionality for linking to the second linking group is attached. The number of heteroatoms in the first linking group, excluding the functionality for linking to the second linking group, usually ranges from about 0 to about 6, usually from about 2 to about 5. Although not required, the portions of the linking groups that lie on either side of the central atom are, in some embodiments, substantially symmetrical. In other words the atoms that extend away from the central atom to the point of attachment of the amphetamine or methamphetamine moiety are the same for each respective portion of the first linking group.

The first linking group may be aliphatic or aromatic. When heteroatoms are present, oxygen will usually be present as oxo or ether bonded to carbon; sulfur is usually present as a thioether or other functionality that corresponds to an analogous oxygen functionality; nitrogen is usually present as nitro, nitroso or amino, normally bonded to carbon; phosphorous is usually bonded to carbon, sulfur, oxygen or nitrogen, usually as phosphonate and phosphate mono- or diester. Common functionalities in forming a covalent bond between the linking group and the molecule to be conjugated, namely, amphetamine and methamphetamine, include alkylamine, amidine, thioamide, ether, urea, thiourea, guanidine, azo, thioether and carboxylate, sulfonate, and phosphate esters, amides and thioesters.

For the most part, the functionality for linking to the second linking group may be a non-oxocarbonyl group including nitrogen and sulfur analogs, a phosphate group, an amino group, a thiol group, a hydroxy group, alkylating agent such as halo or tosylalkyl, oxy (hydroxyl or the sulfur analog, mercapto) oxocarbonyl (e.g., aldehyde or ketone), or active olefin such as a vinyl sulfone or α-,β-unsaturated ester, these functionalities will be linked to amine groups, carboxyl groups, active olefins, alkylating agents, e.g., bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed. Various linking groups and linking functionalities are well known in the art; see, for example, Cautrecasas, *J. Biol. Chem.* (1970) 245:3059.

As mentioned above, a second linking group depends from the first linking group. The second linking group provides for attachment of an attachable moiety such as, for example, a poly(amino acid) or a non-poly(amino acid) label, to form a conjugate in accordance with the present invention. Thus, the second linking group contains a functionality for linking to an attachable moiety. The functionality for linking to the attachable moiety may be, for example, any of the groups mentioned above for the functionality for linking to second linking group, such as, for example, an amine group, a carbonyl group, a hydroxy group, a thiol group, maleimide group, haloacetamide and the like.

The second linking group may be simply a bond to an attachable moiety. The second linking group may be a linking moiety similar in character to the first linking group. An important consideration for the nature and length of the second linking group is that it does not interfere with the recognition, by the respective antibodies, of the amphetamine and methamphetamine moieties in the subsequent bivalent label conjugate to the extent that an accurate and sensitive assay is not obtained. The second linking group may comprise about 1 to about 30 atoms, usually, about 2 to about 25 atoms, about 2 to about 20 atoms, about 4 to about 15 atoms, about 5 to about 10 atoms, not counting hydrogen or a functionality for linking to the attachable moiety. The second linking group usually comprises a chain of from about 1 to about 15 atoms, about 2 to about 12 atoms, about 3 to about 10 atoms, about 4 to about 8 atoms, each independently selected from the group normally consisting of carbon, oxygen, sulfur, nitrogen, halogen and phosphorous, and so forth. The functionality for linking to an attachable moiety is usually at the terminus of the chain of atoms although it need not be. The number of heteroatoms in the second linking group, excluding the functionality for linking to the attachable moiety, usually ranges from about 0 to 10, usually from about 2 to about 8, from about 3 to about 7.

Also included in the above compounds are salts thereof, particularly, salts involving the amine group of the amphetamine and/or methamphetamine. In one embodiment the salts are acid salts, i.e., salts formed with acids such as mineral acids, for example, hydrochloric acid, hydrobromic acid, hydrofluoric acid, hydroiodic acid, phosphoric acid, and the like, organic acids, for example, trifluoroacetic acid, tartaric acid, acetic acid and so forth.

As mentioned above, one of the attachable moieties is a poly(amino acid). Various protein types are included within the term "poly(amino acid)," both natural and synthetic. These proteins include, for example, enzymes, albumins, serum proteins, e.g., globulins, lipoproteins, and the like. The molecular weight of the poly(amino acids) will generally be at least about 5,000 and have no upper limit, normally being less than 10,000,000, and usually being not more than about 600,000. There will usually be different ranges depending on the type of protein involved. With enzymes, the range will be from about 10,000 to 600,000, and more usually from about 10,000 to 300,000 molecular weight. With antigens, the range will be from about 5,000 to 10,000,000, usually from about 20,000 to 600,000, and more usually from about 25,000 to 250,000 molecular weight. There is usually at least about one amphetamine and methamphetamine analog group per 200,000 molecular weight, at least one per 50,000 molecular weight, at least one per 30,000 molecular weight. In the case of enzymes, the number of amphetamine and methamphetamine analog groups is usually from about 1 to about 20, about 2 to about 15, about 3 to about 12, or about 6 to about 10.

Enzymes of particular interest are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

The term "non-poly(amino acid) labels does not include enzyme labels. A non-poly(amino acid) label may be a member of a signal producing system. The non-poly(amino acid) label is capable of being detected directly or is detectable through a specific binding reaction that produces a detectable signal. The non-poly(amino acid) labels generally are radioisotopic, luminescent, particulate, polynucleotidic or the like. More particularly, the label can be isotopic or non-isotopic, usually non-isotopic, and can be a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like.

The signal producing system may have one or more components, at least one component being the label, whether poly(amino acid) or non-poly(amino acid). The signal producing system generates a signal that relates to the presence of an amphetamine and/or methamphetamine in a sample. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Exemplary signal-producing systems are described in U.S. Pat. No. 5,508,178 (Rose, et al.), the relevant disclosure of which is incorporated herein by reference.

As mentioned above, one aspect of the present invention concerns compounds of the formula:

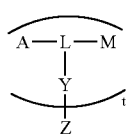

Formula I wherein:
A is an amphetamine moiety such as, for example, an amphetamine analog or derivative thereof, M is a methamphetamine moiety such as, for example, a methamphetamine analog or derivative thereof, L is a linking group, Y is a bond, a functional group or a linking group and is bonded to L at a point equidistant between A and M, and Z is a poly(amino acid) moiety such as, for example, an enzyme, a non-poly(amino acid) label moiety or a functional group;

t is 1 when Z is a functional group or a non-poly(amino acid) label moiety or, when Z is a poly(amino acid), t is an integer between 1 and the molecular weight of a poly(amino acid) moiety divided by about 500.

Salts of the above compounds are also included within the above formula.

Included within the above compounds are compounds of the formula:

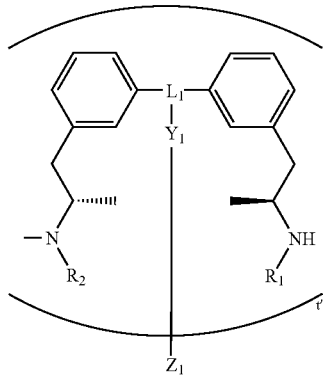

Formula II wherein:
$R_1$ is hydrogen, lower alkyl, protecting group or the like;
$R_2$ is hydrogen, lower alkyl, protecting group or the like;
$L_1$ is a linking group,
$Y_1$ is a bond, a functional group or a linking group and is bonded to L, at a point equidistant between the point of attachment to each of the phenyl groups,
$Z_1$ is a poly(amino acid) moiety such as, for example, an enzyme, a non-poly(amino acid) label moiety or a functional group; and
t' is 1 when $Z_1$ is a functional group or a non-poly(amino acid) label moiety or, when $Z_1$ is a poly(amino acid), t' is an integer between 1 and the molecular weight of a poly(amino acid) moiety divided by about 500.

Also included within the above formula are salts of the above compounds.

By the term "lower alkyl" is meant a branched or unbranched saturated monovalent hydrocarbon radical containing 1 to 10, usually, 1 to 5, carbon atoms, such as methyl, ethyl, propyl, butyl and pentyl, and including the normal, secondary, tertiary, and the like, forms thereof where appropriate.

Another embodiment of the present invention is directed to compounds of the formula:

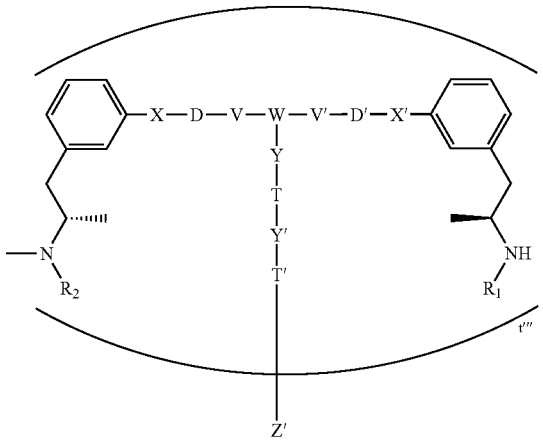

Formula III wherein:
$R_1$ and $R_2$ are independently H, lower alkyl, or a protecting group or the like,
X and X' are independently O, S, or the like, or a bond;
D and D' are independently alkylene or substituted alkylene or the like;
V and V' are independently O, S, or the like, or a bond;
W is CH or the like;
Y is $NR_3$ wherein $R_3$ is H or lower alkyl, O, S, a bond, or the like;
T is alkylene, —(C=O)alkylene, ethereal alkylene, acetamide or a bond;
Y' is $NR_3$ wherein $R_3$ is H or lower alkyl, O, S, or a bond;
T' is alkylene, —(C=O)alkylene, ethereal alkylene, acetamide or a bond; and
Z' is a poly(amino acid), a non-poly(amino acid) label moiety, H, halogen (Br, Cl, F, I), $NH_2$, acetamide, haloacetamide;
t" is 1 when Z' is a functional group or a non-poly(amino acid) label moiety or, when Z' is a ploy(amino acid), t" is an integer between 1 and the molecular weight of a poly(amino acid) moiety divided by about 500;

with the proviso that X and X' have approximately the same length, D and D' have approximately the same length, and V and V' have approximately the same length;

Also included are salts of the above compounds.

"Approximately the same length" means that the lengths of the moieties in question are such that the amphetamine moiety and the methamphetamine moiety are disposed so that they are substantially equally spaced, or equally spaced, apart. In one embodiment, the moieties are equally spaced.

"Alkylene" means a branched or unbranched saturated divalent hydrocarbon radical containing 1 to 30 or more carbon atoms, such as methylene, ethylene, propylene, 2-methylpropylene, 1,2-dimethylpropylene, pentylene, and the like. The term encompasses lower alkylene (1 to 10 carbon atoms) and higher alkylene (11 to 30 carbon atoms).

"Ethereal alkylene" means alkylene having 1 to 10, 1 to 9, 1 to 8, 1 to 7, 1 to 6, 1 to 5, 1 to 4, 1 to 3, 1 to 2, ether functions in the alkylene chain. An example, by way of illustration and not limitation, is —[(CH$_2$)$_a$—O—(CH$_2$)$_a$]$_c$— wherein a and b are independently 1 to 5, 2 to 4, 1 to 3, 1 to 2, or 1, 2, 3, 4, or 5 and wherein c is 1 to 15, 2 to 14, 3 to 13, 4 to 12, 5 to 11, 6 to 10, 7 to 9, or 1, 2, 3, 4, 5, 6, 7, 8, 9, 10, 11, 12, 13, 14 or 15, in particular, —[(CH$_2$)$_a$—O—(CH$_2$)$_a$]$_c$— wherein a and b are 2 and c is as defined above.

"Haloacetamide" means —XCH$_2$—CO—NH$_c$— wherein X is halogen (bromine, chlorine, fluorine, or iodine, usually, bromine or chlorine).

"Substituted" means that a hydrogen atom of a molecule is replaced by another atom, which may be a single atom such as a halogen, or heteroatom, or part of a group of atoms forming, for example, alkyl groups, heteroatom substituted alkyl groups, cyclic structures or heterocyclic structures.

Another embodiment of the present invention is a compound of the formula:

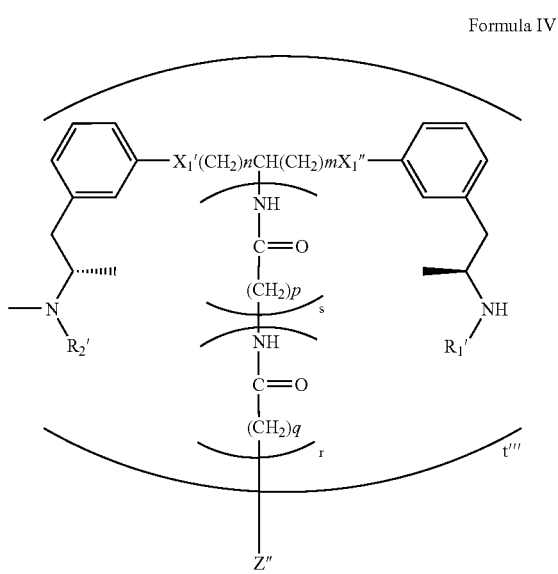

Formula IV wherein:
R$_1$' and R$_2$' are independently H, lower alkyl, a protecting group, or the like,
X$_1$' and X$_1$" are S or O or the like;

Z" is an enzyme; H, Br, Cl, Fl, I, NH$_2$, acetamide, haloacetamide, or the like;

t''' is 1 when Z" is other than an enzyme and, when Z" is an enzyme, t''' is an integer between 1 and the molecular weight of the enzyme divided by about 500; and n, m, p, q are each independently 1 to 5 and r and s are each independently 0 to 5.

The above formula also includes salts thereof.

Another embodiment of the present invention is a compound of the formula:

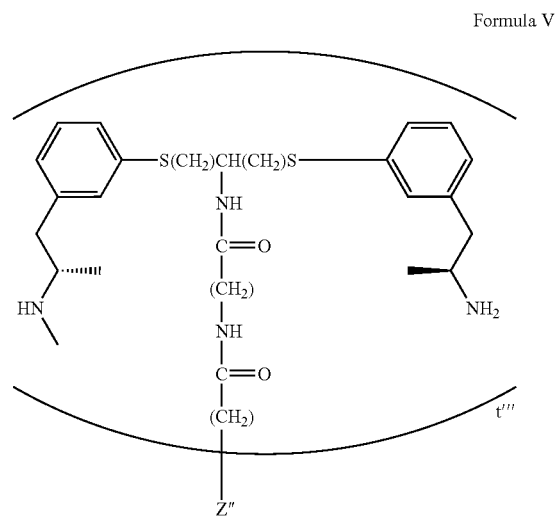

Formula V wherein:
Z" is an enzyme; and
t''' is an integer between 1 and the molecular weight of the enzyme divided by about 500.

The synthesis of representative examples of the above compounds is discussed herein by way of illustration and not limitation. Other synthetic procedures will be suggested to those skilled in the art in view of the disclosure herein. Other compounds within the scope of the present invention may be prepared using suitable variants of the reagents employed below.

Figure 2:
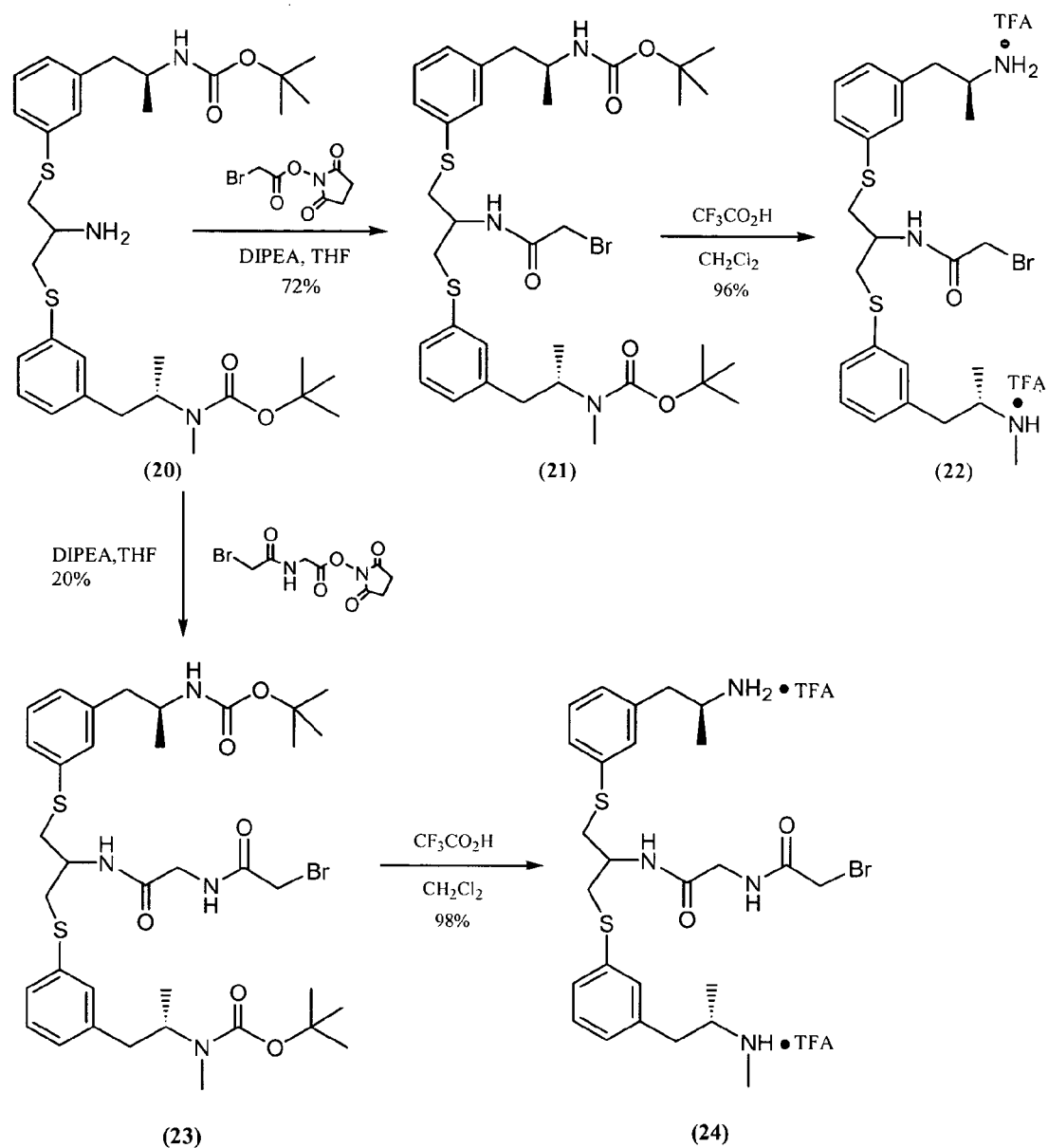
FIG. 2 is a reaction scheme depicting an example of a synthesis of certain compounds in accordance with the present invention.

Stereospecific amphetamine-methamphetamine bivalent hapten linked to an enzyme may be synthesized, for example, by procedures outlined in FIG. 1 and FIG. 2. Protected amphetamine derivative (11) is reacted with protected methamphetamine derivative (18) under conditions for the displacement of the bromine of derivative (11) by the sulfur of derivative (18) to give bivalent compound (19). These conditions are generally basic conditions (pH about 8.0 to about 14.0). Suitable bases include mono-, di-, and tri-alkyl amines such as, for example, diisopropylethyl amine, ethyl amine, diethyl amine, triethyl amine, and the like. The reaction is usually carried out in an organic solvent such as, for example, a ketone, e.g., acetone and the like, an organic ether, e.g., ethyl ether, tetrahydrofuran (THF), dioxane, and the like, an alcohol, e.g., methanol, ethanol, propanol, and the like. The reaction temperature is usually about 0° C. to about 50° C., more usually, about 10° C. to about 30° C., preferably, ambient temperature. The reaction is carried out for a period of about 10 minutes to about 3 hours or more, usually, about 30 minutes to about 60 minutes.

The keto functionality of compound (19) is converted by reductive amination to an amine functionality to produce compound (20). The reaction is conducted in an organic solvent such as aqueous alcohol, Suitable reagent include ammonium acetate and the like. A reducing agent such as a metal hydride, for example, NaBH$_3$CN and the like may be employed. The reaction temperature is usually about 0° C. to about 50° C., more usually, about 10° C. to about 30° C., preferably, ambient temperature. The reaction is carried out for a period of about 1 hour to about 16 hours or more.

For the preparation of compound (21), compound (20) is reacted with an activated ester of bromoacetic acid, namely, the N-hydroxy succinimide ester of bromoacetic acid in this example, under basic conditions, which include incorporating into the reaction mixture an alkyl amine such as, for example, diisopropylethylamine, ethylamine, triethyl amine, and the like. The reaction is conducted in an organic solvent such as, for example, an ether, e.g., THF, Dioxane, diethyl ether and so forth. The reaction is usually carried out at a temperature of about 0° C. to about 50° C., more usually, about 10° C. to about 30° C., preferably, ambient temperature. The reaction is carried out for a period of about 30 minutes to about 5 hours or more, usually, about 1 hour to about 3 hours or more.

The protecting group of compound (21) may be removed under acidic conditions in an organic solvent to give compound (22). In the example depicted, compound (21) is treated with trifluoroacetic acid (TFA) in methylene chloride. In general, removal of the protecting group is dependent on the nature of the protecting group. Suitable conditions for removal of protecting groups are well known in the art and will not be discussed in detail herein.

Compound (20) may also be converted into compound (23) by reaction with an activated ester of bromoacetylglycine, namely, the N-hydroxy succinimide ester in the example shown in FIG. 2. The reaction is carried out under basic conditions with an organic solvent. The basic conditions include incorporating into the reaction mixture an alkyl amine such as, for example, diisopropylethylamine, ethylamine, triethyl amine, and the like. The reaction is conducted in an organic solvent such as, for example, an ether, e.g., THF, dioxane, diethyl ether, and so forth. The reaction is usually carried out at a temperature of about 0° C. to about 50° C., more usually, about 10° C. to about 30° C., preferably, ambient temperature. The reaction time is a period of about 30 minutes to about 5 hours or more, usually, about 1 hour to about 3 hours or more. The protecting groups of compound (23) may be removed as discussed above to produce compound (24).

Any of the compounds discussed above may be purified by known techniques such as, for example, dialysis, chromatography, HPLC, and combinations thereof.

Enzyme conjugates may be prepared from compounds in accordance with the present invention. In general, functional groups suitable for attaching the compound to the enzyme are usually an activated ester or alkylating agent when the amino acid(s) that are to be conjugated on the enzyme have amino or hydroxyl groups and are usually alkylating agents or the like when the amino acid(s) that are to be conjugated on the enzyme comprise a sulfur atom such as, e.g., a cysteine. A large number of suitable functional groups are available for attaching to amino groups and alcohols such as activated esters including imidic esters, sulfonic esters and phosphate esters, activated nitriles, aldehydes, ketones, alkylating agents and the like. Conjugation of haptens to proteins using these and other attaching groups are well known in the art and are described in reviews such as for example, Maggio, E. T. "Enzyme-Immunoassay" (CRC Press, Boca Raton, Fla., 1980), Chapter 4, which contains an assortment of conjugation techniques; pages 81–88 of which are incorporated herein by reference.

Following reaction of the enzyme with a compound such as discussed above to form a conjugate, the product is then optionally purified as may be required. The purification and characterization of poly(amino acid)-hapten conjugates has been described in detail Maggio, et al.; "enzyme-immunoassay" (CRC Press, Boca Raton, Fla., 1980), Chapter 4, pages 86–88 of which are incorporated herein by reference. For example, if the conjugate is a mutant G6PDH-hapten conjugate, the purification can be by dialysis against aqueous/organic and aqueous solutions such as water/DMF or water, or by gel filtration chromatography on supports such as Sephadex, and the like.

As mentioned above, the conjugation can involve binding of a hapten to a free thiol group present on an amino acid side chain of the enzyme (e.g. cysteine). Such conjugation involves alkylation of the thiol sulfur atom by treatment with an electrophilic compound such as an alpha- or beta-unsaturated amide, ketone, ester, or the like, or an alkylating agent such as a reactive halide, e.g., bromide, or sulfonate or the like or reaction with an active disulfide such as a 2-nitro-4-carboxyphenyl disulfide. Specific examples by way of illustration and not limitation include alpha-bromoamides, maleimides, vinyl sulfones, alpha-iodoketones, and the like.

Conjugation reactions with enzymes can be affected by a number of factors. These include, but are not confined to, pH, temperature, buffer, ionic strength, substances which may protect the enzyme active site, amount and type of cosolvent, reaction time, and activation chemistry. A range of pH values from about 5.0 to about 9.5 can usually be used for conjugation reactions. These reactions are generally carried out at about 0 to about 40 degrees C., preferably about 4 to about 20 degrees C.

A number of buffers and salts, both alone and in combination, can be used for such reactions. These include Tris, bicarbonate, phosphate, pyrophosphate, EDTA, KCl, NaCl, and many others. The active site may be protected by substrates (i.e. glucose-6-phosphate for glucose-6-phosphate dehydrogenase), cofactors (NAD$^+$, NADH, NADP$^+$, NADPH) and cofactor analogs (thio-NAD$^+$, thio-NADH, thio-NADP$^+$, or thio-NADPH), and compounds that react reversibly with lysine (i.e. pyridoxal) to reduce deactivation of the enzyme during conjugation.

Cosolvents which may enhance hapten solubility include, but are not limited to, dimethylformamide, carbitol, dimethyl sulfoxide, 1-Methyl-2-pyrrolidinone, and 1,3-Dimethyl-3,4,5,6-tetrahydro 2(1H)-pyrimidinone. These may be useful as about 1 to about 30% of the reaction volume. Reactions can vary from about 15 minutes to many days, depending on the activation chemistry. Carboxylic compounds may be activated to form esters with N-Hydroxysuccinimide or its sulfo-analog, or to mixed anhydrides through reaction with carbitol chloroformate or t-butylchloroformate, or may be coupled directly using carbodiimides such as EDAC. For reaction with cysteine thiols on the enzyme, the hapten should contain a good leaving group such as I, Br or tosyl; alternatively, the hapten can contain a thiol, preferably activated with 2,2' dithiodipyridine or DTNB.

Another method of conjugation, described in Rowley, G. L., D. Leung, and P. Singh (U.S. Pat. No. 4,220,722) involves modification of the enzyme with bromoacetyl containing reactants; the bromo groups are subsequently reacted with thiol-containing haptens. The reactions of enzyme with bromoacetyl modifier and the bromoacetyl enzyme with the thiolated hapten are subject to the same reaction condition variables described above.

Enzyme conjugates may be prepared using compound (22) or compound (24). For example, conjugates comprising glucose-6-phosphate dehydrogenase may be prepared by procedures known in the art. These procedures generally involve displacement of the bromine of compound (22) or compound (24) by a sulfur of a cysteine group of the enzyme. Since the enzyme has multiple cysteine groups, more than one molecule of compound (22) or compound (24) usually becomes conjugated to the enzyme.

The label conjugates of the present invention may be employed in various assay formats. Such assays usually involve reactions between binding partners such as an amphetamine analyte and/or a methamphetamine analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

The aforementioned reagents may be employed in all types of immunoassays to determine the presence and/or amount of amphetamine analytes and/or methamphetamine analytes in a sample suspected of containing such analytes. Such assays include, for example, enzyme immunoassays, fluorescence polarization immunoassays, radioimmunoassay, particle enhanced turbidimetric inhibition immunoassay and so forth.

One general group of immunoassays includes immunoassays using the labeled conjugates of the invention with a limited concentration of antibody. Another group of immunoassays involves the use of an excess of all of the principal reagents. Such assays include two-site sandwich assays, e.g., immunoradiometric assays, immunofluorometric assays, immunochemi-luminometric assays, ELISA assays, and so forth. Another group of immunoassays are separation-free homogeneous assays in which the labeled reagents modulate the label signal upon antigen-antibody binding reactions. Another group of assays includes labeled antibody reagent limited competitive assays for hapten or antigen that avoid the use of problematic labeled antigens or haptens. In this type of assay, it is important that the solid phase immobilized analyte be present in a constant, limited amount. The partition of a label between the immobilized analyte and free analyte depends on the concentration of analyte in the sample.

The label conjugates of the invention may be employed with antibodies to amphetamine and methamphetamine to conduct an immunoassay for the amphetamine and methamphetamine analytes. The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285–288; the substrate labeled fluorescence immunoassay ("SLFIA") disclosed by Oellerich, J. Clin. Chem. Clin. Biochem. (1984) 22:895–904; the combined enzyme donor immunoassays ("CEDIA") disclosed by Khanna, et al., Clin. Chem. Acta (1989) 185:231–240; homogeneous particle labeled immunoassays such as particle enhanced turbidimetric inhibition immunoassays ("PETINIA"), particle enhanced turbidimetric immunoassay ("PETIA"), etc.; and the like.

Exemplary of heterogeneous assays are the enzyme linked immunosorbant assay ("ELISA") discussed in Maggio, E. T. supra; the radioimmunoassay, disclosed in Yalow, et al., J. Clin. Invest. 39:1157 (1960) and so forth.

The above reagents may also be employed in multi-analyte immunoassays where the amphetamine and/or methamphetamine analytes may be the subject of detection along with one or more other analytes such as other drugs of abuse and the like. Such multi-analyte systems are discussed, for example, in an article from Microgenics Corporation, entitled "Multiplex assay of amphetamine, methamphetamine and ecstasy drug using CEDIA technology" (J Anal. Toxicol., 2002, vol, 26, page, 267).

The homogeneous or heterogeneous assays, particularly enzyme immunoassays and fluorescence polarization immunoassays, are normally carried out in an aqueous buffered medium at a moderate pH, generally that which provides optimum assay sensitivity. The aqueous medium may be solely water or may include from 0 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the method in accordance with the present invention. For example, in addition to buffers the medium may comprise stabilizers for the medium and for the reagents employed. Frequently, in addition to these additives, proteins may be included, such as albumins; organic solvents such as formamide; quaternary ammonium salts;

polyanions such as dextran sulfate; surfactants, particularly non-ionic surfactants; binding enhancers, e.g., polyalkylene glycols; or the like.

One or more incubation periods may be applied to the medium at one or more intervals including any intervals between addition of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 6 hours, usually, from about 2 seconds to about 1 hour, more usually, about 1 to about 5 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., more usually from about 15 to about 40° C.

The concentration of analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents.

The concentration of analytes to be detected will generally vary from about $10^{-5}$ to about $10^{-17}$ M, more usually from about $10^{-6}$ to about $10^{-14}$ M. In general, a predetermined cut-off level is established for each analyte suspected of being in a sample. The particular predetermined cut-off level generally is determined on an analyte by analyte basis. Those skilled in the art are well aware of the factors relating to the selection of predetermined cut-off levels. For example, for many drugs of abuse, the cut-off levels are determined by SAMSA, an agency of the Department of Health and Human Services. The nature of the signal producing system may be a consideration in determining the predetermined cut-off levels of some analytes. Another consideration is that the expected variation in concentration of the analytes that is of significance should provide an accurately measurable signal difference.

The concentrations of the various reagents in the assay medium will generally be determined by the concentration range of interest of the amphetamine and/or the methamphetamine analytes. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of, and predetermined cut-off levels for, the analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition, generally ranging from about 30 seconds to about 6 hours, more usually from about 1 minute to about 1 hour.

The following examples further describe the specific embodiments of the invention by way of illustration and not limitation and are intended to describe and not to limit the scope of the invention.

In a homogeneous assay after all of the reagents have been combined, the signal is determined and related to the amount of analyte in the sample. For example, in an EMIT assay for amphetamine and/or methamphetamine, a sample suspected of containing amphetamine and/or methamphetamine analytes is combined in an aqueous medium either simultaneously or sequentially with an enzyme conjugate of the invention and antibody capable of recognizing amphetamine and antibody capable of recognizing methamphetamine where the antibodies also bind to the respective amphetamine and methamphetamine moieties of the enzyme conjugate prepared in accordance with the present invention. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The analytes and the moieties of the enzyme conjugate compete for binding sites on the antibody. The enzyme activity in the medium is then determined, usually by spectrophotometric means, and is compared to the enzyme activity determined when calibrators or reference samples are tested in which a known amount of the analytes is present. Typically, the calibrators are tested in a manner similar to the testing of the sample suspected of containing the analytes. The calibrators typically contain differing, but known, concentrations of the analyte to be determined. Preferably, the concentration ranges present in the calibrators span the range of suspected analyte concentrations in the unknown samples.

The antibodies specific for amphetamine and specific for methamphetamine for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In another approach for the preparation of antibodies the sequence coding for antibody binding sites can be excised from the chromosome DNA and inserted into a cloning vector, which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using amphetamine antibodies and methamphetamine antibodies as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. In one type of competitive assay a support having antibodies for amphetamine and for methamphetamine bound thereto is contacted with a medium containing the sample and an enzyme conjugate of the invention. After separating the support and the medium, the enzyme activity of the support or the medium is determined by conventional techniques and related to the amount of amphetamine and/or methamphetamine in the sample.

The support may be comprised of an organic or inorganic, solid or fluid, water insoluble material, which may be transparent or partially transparent. The support can have any of a number of shapes, such as particle, including bead, film, membrane, tube, well, strip, rod, plate and the like. Depending on the type of assay, the support may or may not be suspendable in the medium in which it is employed. Examples of suspendable supports are polymeric materials such as latex, lipid bilayers or liposomes, oil droplets, cells and hydrogels. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

Binding of components to the surface of a support may be direct or indirect, covalent or non-covalent and can be accomplished by well-known techniques, commonly available in the literature, as discussed above. See, for example, "Immobilized Enzymes," Ichiro Chibata, Halsted Press, New York (1978) and Cautrecasas, *J. Biol. Chem.*, 245:3059 (1970). The surface of the support is usually polyfunctional or be capable of being polyfunctionalized or be capable of binding to an sbp member, or the like, through covalent or specific or non-specific non-covalent interactions. Such binding is indirect where non-covalent interactions are used and is direct where covalent interactions are employed. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above).

Activation of the signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems addition of a substrate and/or a cofactor may be necessary.

In certain embodiments a second enzyme may be employed in addition to the enzyme of the enzyme conjugate. The enzymes of the pair of enzymes are related in that a product of the first enzyme serves as a substrate for the second enzyme.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the amphetamine and/or methamphetamine analytes present in a sample above the predetermined cut-off level. Temperatures during measurements generally range from about 10° to about 70° C., more usually from about 20° to about 45° C., more usually about 20° to about 25° C. In one approach standard curves are formed using known concentrations of the analytes to be screened. As discussed above, calibrators and other controls may also be used.

Another aspect of the present invention relates to kits useful for conveniently performing an assay for the determination of amphetamine and/or methamphetamine analytes. The kit comprises in packaged combination (i) an antibody for amphetamine, (ii) an antibody for methamphetamine, and (iii) a compound of Formula I wherein the compound comprises a label such as an enzyme. Any of the compounds discussed above may form part of the kit as the compound of Formula I.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

EXAMPLES

The invention is demonstrated further by the following illustrative examples. Parts and percentages recited herein are by weight unless otherwise specified. Temperatures are in degrees centigrade (° C.).

Analytical thin layer chromatography (TLC) was the usual analysis method and performed on Analtech Uniplate Silica Gel GF (0.25 mm) glass-backed plates using the specified solvent. The spots on TLC were visualized by ultraviolet light (short and/or long wave) and/or iodine vapors. Flash chromatography was carried out on Whatman silica gel 60 Å (230–400 mesh). All chemicals were obtained from Sigma Chemical Company (St. Louis, Mo.), Aldrich Chemical Company (St. Louis, Mo.), Fluka (Milwaukee, Wis.), and Lancaster and used as received. $^1$H-NMR and $^{13}$C-NMR spectra routinely recorded on a Bruker Ultrashiel™-400 (400 MHz) spectrometer (Bruker; Bellerica, Mass. 01821). Chemical shifts were reported in parts per million (ppm, δ) and related to tetramethylsilane or with deuterated solvent as internal reference. NMR abbreviations used are s (singlet), d (doublet), and m (multiplet). Mass spectra were obtained at the Mass Spectrometry Laboratory, University of California at Berkeley, Berkeley, Calif.

UV-visible absorption spectra were done on a HP 8452A diode array spectrophotometer. Fluorescence measurements were done on a Spex fluorolog spectrophotometer or a Perkin Elmer 650-40 spectrophotometer.

The following abbreviations have the meanings set forth below:
18-crown-6: 1,4,7,10,13,16-hexaoxacyclooctadecane
EtOH—ethanol
g—grams
MeI—iodomethane
ml—milliliter
mmol—millimolar
Pd/C—10% Palladium on activated charcoal
DMF—dimethyl formamide
THF—tetrahydrofuran
NMR—nuclear magnetic resonance spectroscopy
MHz—megahertz
EDAC—1-ethyl-3-(3-dimethylaminopropyl)carbodiimide hydrochloride (Sigma Chemical Company)
MeOH—methanol
FAB-MS—fast atom bombardment—mass spectrometry
FAB-HRMS—fast atom bombardment—high resolution mass spectrometry
EI-MS—electron impact mass spectroscopy
EI-HRMS—electron impact high resolution mass spectroscopy
DI water—deionized water
TNBS—2,4,6-trinitorbenzesulfonic acid
NHS—N-hydroxysuccinimic ester
tBoc$_2$O—di-tert-butyldicarbonate
TFA—trifluoroacetic acid Preparation of Antibodies The antibodies used in the experiments herein were monoclonal antibodies prepared as described in U.S. Pat. Nos. 5,328,828 and 5,135,863, the relevant disclosures of which have been incorporated hereinabove by reference. In particular, see, for example, column 37, line 16, to column 39, line 55, of U.S. Pat. No. 5,135,863.

In general, the monoclonal antibodies were produced according to the standard techniques of Köhler and Milstein, Nature 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of an non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

Preparation of Compound (11)

Figure 7:
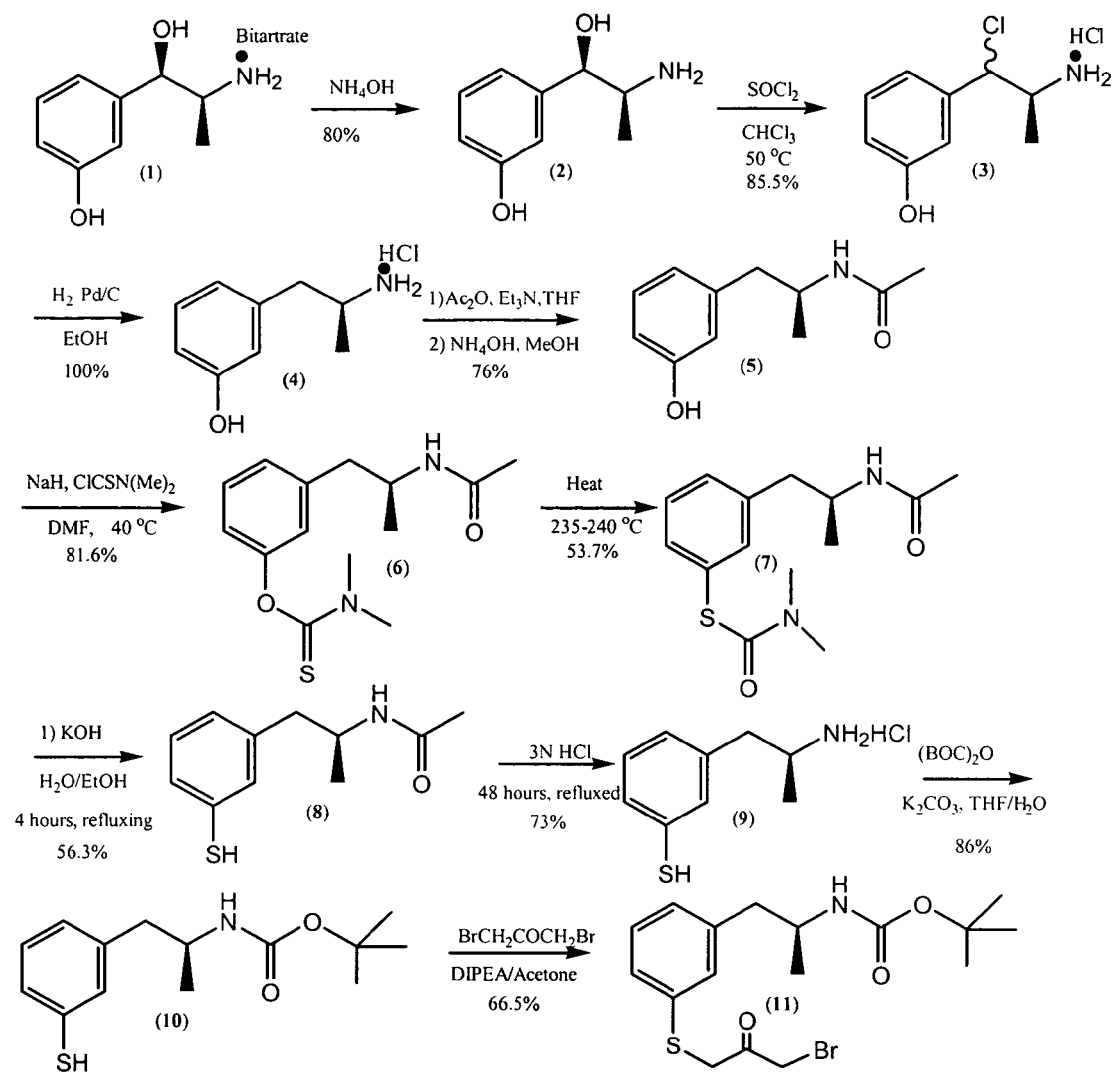
FIG. 7 is a reaction scheme depicting an example of a synthesis of certain compounds used in the synthesis of compounds in accordance with the present invention.

Compound (11) was prepared starting with compound (1) as described below (see also FIG. 7).

Preparation of Metaraminol (2)

To a solution of [−]-m-hydroxyphenyl propanolamine bitartrate salt (1) (40 g, 126 mmol) in water (60 ml) was added slowly of $NH_4OH$ (60 ml). The mixture was stirred at room temperature for 0.5 hour. The mixture was extracted with ethyl acetate (6×250 ml). The combined organic phase was washed with water (30 ml) and dried over anhydrous $MgSO_4$. The organic solvent was filtered and the filtrate was evaporated by rotary evaporation followed by high vacuum to dryness to give the desired product metaraminol (2) (16.8 g, 79.7% yield). This product was used for next reaction without further purification.

Preparation of Compound (3)

To a stirred solution of metaraminol (2) (16.8 g, 100.4 mmol) in chloroform (250 ml) was added slowly thionyl chloride (60 ml, 800 mmol) under argon. The reaction mixture was stirred for 0.5 hour and was heated at 50° C. for 45 minutes using an oil bath. The reaction mixture was cooled to room temperature. The chloroform and most of excess thionyl chloride were removed by rotary evaporation under high vacuum. After the evaporation, a crude solid residue was formed. The solid residue was dissolved in MeOH (250 ml) and heated with charcoal (30 g) at 70° C. by a water bath for 0.5 hour. The hot MeOH solution was filtered through a celite pad (0.5 cm thickness) on a filtering funnel. The filtrate was evaporated by rotary evaporation followed by high vacuum to dryness to give the desired product (3) (19.0 g, 85.5% yield). This product was used for the next reaction without further purification.

Preparation of Compound (4)

To a stirred solution of (3) (19.0 g, 85.54 mmol) in EtOH (100 ml) was added 10% Pd/C (7.0 g) and the solution was hydrogenated at a hydrogenator (parr) under 35 psi pressure of hydrogen for 16 hours. The ethanol solution was filtered through a celite pad (0.5 cm thickness) and the celite pad was washed with EtOH (30 ml). The combined filtrates were evaporated by rotary evaporation followed by high vacuum to dryness to give the desired product, (2S)-3-(2-aminopropyl)phenol hydrochloride (4) (16.1 g, 100% yield). $^1$H-NMR ($CD_3OD$, 400 MHz) δ: 7.15 (m, 1H), 6.90 (m, 3H), 3.48 (m, 1H), 2.85 (m, 1H), 2.70 (m, 1H), 1.24 (d, J=6.6 Hz, 3H). This product was used for next reaction without further purification.

Preparation of Compound (5)

To a stirred solution of (4) (5 g, 26.64 mmol) in THF (150 ml) was added slowly of triethylamine (3.8 ml, 27.2 mmol). The reaction mixture was stirred at room temperature for 10 minutes. Acetic anhydride (2.6 ml, 27.51 mmol) was added into the mixture followed by potassium carbonate (3.68 g, 26.63 mmol). The reaction mixture was stirred at room temperature for 3 hours. Water (50 ml) was added and most of THF was evaporated by rotary evaporation. The aqueous phase was extracted with ethyl acetate (4×120 ml). The combined organic phases were washed with water (40 ml) and dried over $MgSO_4$. The organic phase was evaporated to dryness by rotary evaporation and the residue was dissolved in methanol (40 ml) and $NH_4OH$ (10 ml). The solution was stirred at room temperature for 0.5 hour and most of methanol was removed by rotary evaporation. Water (20 ml) was added and the aqueous phase was extracted with ethyl acetate (4×50 ml). The combined extracts were washed with water (15 ml) and dried over $MgSO_4$. The organic solvent was filtered and evaporated to dryness by rotary evaporation. The residue was purified by flash column chromatography (silica gel) using ethyl acetate/hexane (4/1) as an eluent to give acetamine (5) (3.90 g, 76% yield). $^1$H-NMR ($CDCl_3$, 400 MHz) δ:7.91 (m, 1H, OH), 7.12 (m, 1H), 6.77 (m, 2H), 6.68 (m, 1H), 5.61 (m, 1H, NH), 4.28 (s, 1H), 2.81 (m, 1H), 2.66 (m, 1H), 1.98 (s, 3H), 1.13 (d, J=6.5 Hz, 3H).

Preparation of Compound (6)

To a stirred solution of (5) (2.45 g, 12.68 mmol) in DMF (80 ml) was added NaH (0.5 g, 95%, 19.79 mmol) at 0° C. The reaction mixture was stirred at room temperature for 45 minutes under argon. After hydrogen evolution ceased, the reaction mixture was cooled to 0° C. and dimethylthiocarbamoyl chloride (2.35 g, 19.0 mmol) was added into the mixture. The reaction mixture was stirred and heated at 45° C. for 2 hours and allowed to cool to room temperature. Saturated sodium chloride solution (50 ml) and water (30 ml) were added to the mixture. The aqueous phase was extracted with ethyl acetate (3×100 ml) and the combined organic phase was washed with saturated NaCl solution (50 ml) and dried over $MgSO_4$. The organic solvent was filtered and evaporated to dryness by rotary evaporation. The residue was purified by flash column chromatography (silica gel) using ethyl acetate/hexane (9/1) as an eluent to give (6) (2.9 g, 81.6% yield). $^1$H-NMR ($CDCl_3$, 400 MHz) δ: 7.30 (m, 1H), 7.05 (m, 1H), 6.90 (m, 2H), 5.36 (m, 1H, NH), 4.30 (m, 1H), 3.44 (s, 3H), 3.34 (s, 3H), 2.79 (m, 2H), 1.93 (s, 3H), 1.09 (d, J=6.4 Hz, 3H).

Preparation of Compound (7)

Neat compound (6) (2.14 g, 7.60 mmol) was stirred and heated under argon at 238–243° C. in an oil bath for 8 hours. The complete reaction was observed by thin layer chromatography (TLC) (silica gel, ethyl acetate) by the disappearance of one spot and a new spot displayed on TLC. The reaction was allowed to cool to room temperature. The oily residue was purified by flash column chromatography (silica gel) using ethyl acetate as an eluent to give (7) (1.15 g, 53.7% yield). $^1$H-NMR ($CDCl_3$, 400 MHz) δ: 7.32–7.28 (m, 3H), 7.18 (m, 1H), 5.67 (m, 1H, NH), 4.25 (m, 1H), 3.08 (s, 3H), 3.00 (s, 3H), 2.78 (m, 2H), 1.93 (s, 3H), 1.05 (d, J=6.6 Hz, 3H); $^{13}$C-NMR ($CDCl_3$, 100 MHz) δ: 170.09, 167.31, 139.09, 137.27, 133.71, 130.76, 129.11, 128.92, 46.02, 42.14, 37.30, 23.62, 20.08.

Preparation of Compound (8)

A mixture of (7) (100 mg, 0.356 mmol) and KOH (400 mg, 7.13 mmol) in EtOH (9 ml) and water (6 ml) was refluxed under argon for 4 hours. Most of ethanol was evaporated and water (14 ml) was added to the mixture. The aqueous solution was acidified with 6N HCl (pH about 3) and then extracted with ethyl acetate (4×40 ml). The combined extracts were dried over $MgSO_4$, filtered, and evaporated to dryness by rotary evaporation. The residue was purified by flash column chromatography (silica gel) using ethyl acetate/hexane (9/1) as an eluent to give (8) (42 mg, 56.3% yield). FAB-MS: MH$^+$ (210); $^1$H-NMR ($CDCl_3$, 400 MHz) δ: 7.15–7.07 (m, 3H), 6.93 (m, 1H), 5.57 (m, 1H, NH), 4.20 (m, 1H), 3.42 (s, 1H, SH), 2.75 (m, 1H), 2.58 (m, 1H), 1.91 (s, 3H), 1.07 (d, J=6.6 Hz, 3H).

Preparation of Compound (9)

Compound (8) (206 mg, 0.984 mmol) in 3N HCl (30 ml) was refluxed under argon for 48 hours. The complete reaction was observed by thin layer chromatography (TLC) (silica gel, ethyl acetate/hexane=1/9). The reaction mixture was evaporated by rotary evaporation under high vacuum to dryness. The residues were dissolved in water (5 ml). The aqueous solution was frozen under argon and lyophilized to give (9) (192 mg, 95% yield). FAB-MS: MH+ (168); $^1$H-NMR (D$_2$O, 400 MHz) δ: 7.29–7.08 (m, 3H), 6.95 (m, 1H), 3.40 (m, 1H), 2.76 (m, 2H), 1.06 (d, J=6.6 Hz, 3H); $^{13}$C-NMR (D$_2$O, 100 MHz) δ: 137.78, 132.10, 130.32, 130.00, 128.12, 127.11, 49.53, 40.30, 18.07.

Preparation of Compound (10)

To a stirred solution of (9) (192 mg, 0.942 mmol) in THF (12 ml) and water (6 ml) was added Di-tert-butyl-dicarbonate (420 mg, 1.92 mmol) at 0° C. The reaction mixture was stirred at room temperature for 2 hours under argon. Water (14 ml) was added to the mixture and most of THF was evaporated by rotary evaporation. The aqueous phase was extracted with ethyl acetate (3×70 ml) and the combined organic phase was washed with saturated NaCl solution (30 ml) and dried over MgSO$_4$. The organic solvent was filtered and evaporated to dryness. The residue was purified by flash column chromatography (silica gel) using ethyl acetate/hexane (1/4) as an eluent to give (10) (118 mg, 47% yield) and its disulfide dimer (10a) (98 mg, 20% yield). (10a): FAB-MS: (MH$^-$, 533); $^1$H-NMR(CDCl$_3$, 400 MHz) δ: 7.34–7.18 (m, 6H), 7.04–7.02 (m, 2H), 4.34 (m, 2H, NH), 3.80 (m, 2H), 2.75 (m, 2H), 2.62 (m, 2H), 1.40 (s, 18H), 1.03 (d, J=6.6 Hz, 6H). (10): EI-MS m/z: 267 (M$^+$, 31), 211 (38), 194 (7), 151 (5), 144 (17), 123 (13), 88 (32), 57(100); $^1$H-NMR(CDCl$_3$, 400 MHz) δ: 7.15–7.08 (m, 3H), 6.95 (m, 1H), 4.38 (m, 1H, NH), 3.85 (m, 1H), 3.41(s, 1H, SH), 2.76 (m, 1H), 2.62 (m, 1H), 1.42 (s, 9H), 1.06 (d, J=6.6 Hz, 3H); $^{13}$C-NMR (CDCl$_3$, 100 MHz) δ: 155.56, 139.84, 131.07, 130.72, 129.43, 127.68, 127.26, 79.62, 47.79, 43.17, 28.83, 20.52.

Preparation of Monomer (10) from its Disulfide Dimer (10a)

To a stirred solution of dimer (10a) (138 mg, 0.259 mmol) in THF (8 ml) and NaOAc/AcOH buffer solution (5 ml, pH=5.0) was added Tris-(2-carboxyethyl) phosphine hydrochloride (76 mg, 0.265 mmol). The reaction mixture was stirred at room temperature for 0.5 hour under argon. Most of THF was evaporated by rotary evaporation and the aqueous phase was extracted with ethyl acetate (3×30 ml). The combined organic phase was washed with saturated NaCl solution (20 ml) and dried over MgSO$_4$. The organic solvent was filtered and evaporated to dryness. The residue was purified by flash column chromatography (silica gel) using ethyl acetate/hexane (1/4) as an eluent to give (10) (130 mg, 94% yield).

Preparation of Compound (11)

To a stirred solution of 1,3-dibromoacetone (144 mg, 0.667 mmol) in acetone (5 ml) at 0° C. under argon was added compound (10) (20 mg, 0.0748 mmol) and diisopropyl ethyl amine (14 μl 0.08 mmol). The reaction mixture was stirred at 0° C. for 45 minutes under argon. Acetone was evaporated to dryness by rotary evaporation. The residue was purified by flash column chromatography (silica gel) using ethyl acetate/hexane (1/4) as an eluent to give (11) (20 mg, 66.5% yield). EI-MS m/z: 403(M$^+$, 52), 401 (M$^+$, 50), 347 (74), 345 (72), 330 (44), 328 (40), 260 (14), 258 (16), 144 (100), 88 (31), 57 (100); $^1$H-NMR(CDCl$_3$, 400 MHz) δ: 7.21–7.00 (m, 4H), 4.45 (m, 1H, NH), 4.07 (s, 2H), 3.87 (brs, 3H), 2.80 (m, 1H), 2.65 (m, 1H), 1.41 (s, 9H), 1.05 (d, J=6.4 Hz, 3H); $^{13}$C-NMR (CDCl$_3$, 100 MHz) δ: 197.05, 155.53, 140.06, 133.82, 131.69, 129.67, 129.26, 128.53, 79.62, 47.68, 43.09, 41.52, 32.47, 28.83, 20.47.

Preparation of Compound (18)

Figure 8:
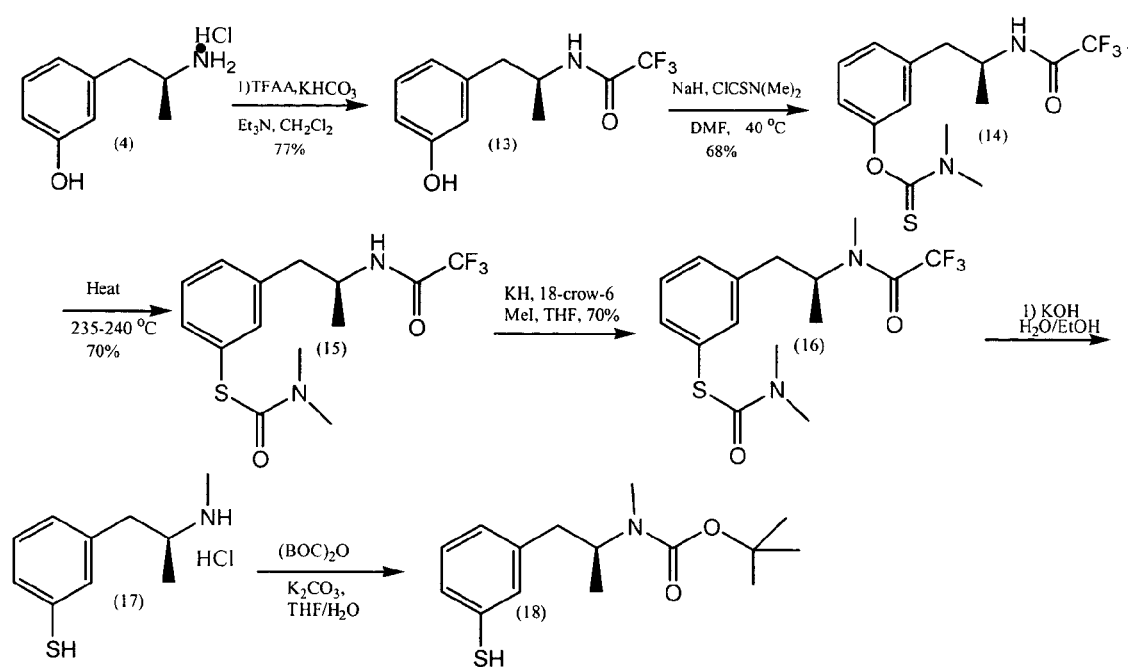
FIG. 8 is a reaction scheme depicting an example of a synthesis of certain compounds used in the synthesis of compounds in accordance with the present invention.

Compound (2) was prepared starting with compound (4) as described below (see also FIG. 8).

Preparation of Compound (13)

To a stirred solution of (4) (271 mg, 1.44 mmol) in CH$_2$Cl$_2$ (30 ml) was added KHCO$_3$ (144 mg, 1.44 mmol) followed by adding slowly triethylamine (0.8 ml, 5.73 mmol). The reaction mixture was stirred at room temperature for 20 minutes. Trifluoroacetic anhydride (0.6 ml, 4.24 mmol) was added into the mixture. The reaction mixture was stirred at room temperature for 4 hours. Water (15 ml) was added and the organic phase was separated. The aqueous phase was extracted with CH$_2$Cl$_2$ (4×30 ml). The combined organic phase were washed with 10% NaHCO$_3$ solution (30 ml) and dried over MgSO$_4$. The organic phase was filtered and evaporated to dryness by rotary evaporation. The residue was purified by flash column chromatography (silica gel) using ethyl acetate/hexane (2/3) as an eluent to give (13) (274 mg, 77% yield). FAB-MS:MH$^+$ (248, 100%); $^1$H-NMR (CDCl$_3$, 400 MHz) δ: 7.17–7.14 (m, 1H), 6.74–6.64 (m, 3H), 6.34 (m, 1H, NH), 5.91 (m, 1H, OH), 4.25 (m, 1H), 2.80–2.73 (m, 2H), 1.20 (d, J=5.9 Hz, 3H). This reaction was repeated by using 10.9 g of (4) and 8.6 g of (13) was obtained. The $^1$H-NMR of (13) in both lots is identical.

Preparation of Compound (14)

To a stirred solution of (13) (1.65 g, 6.67 mmol) in DMF (30 ml) under argon was added NaH (332 mg, 95%, 13.14 mmol) at 0° C. The reaction mixture was stirred at 0° C. for 10 minutes and at room temperature for 45 minutes. After hydrogen evolution ceased, the reaction mixture was cooled to 0° C. and dimethylthiocarbamoyl chloride (1.23 g, 9.95 mmol) was added. The reaction mixture was stirred and heated at 40° C. for 2 hours and allowed to cool to room temperature. Saturated sodium chloride solution (15 ml) and water (35 ml) was added to the mixture. The aqueous phase was extracted with ethyl acetate (4×80 ml) and the combined organic phase were washed with saturated NaCl solution (50 ml) and dried over MgSO$_4$. The organic solvent was filtered and evaporated to dryness by rotary evaporation. The residue was purified by flash column chromatography (silica gel) using ethyl acetate/hexane (3/7) as an eluent to give (14) (1.12 g, 68% yield). $^1$H-NMR (CDCl$_3$, 400 MHz) δ: 7.25 (m, 1H), 7.00 (m, 2H), 6.90 (m, 1H), 6.81 (m, 1H, NH), 4.20 (m, 1H), 3.36 (s, 3H), 3.24 (s, 3H), 2.85 (m, 1H), 2.72 (m, 1H), 1.15 (d, J=6.7 Hz, 3H); $^{13}$C-NMR (CDCl$_3$, 100 MHz) δ: 187.93, 157.06, 154.51, 138.89, 129.60, 127.17, 124.19, 121.48, 47.91, 43.54, 41.79, 39.07, 19.56. HRFAB-MS Calcd for C$_{14}$H$_{18}$F$_3$N$_2$O$_2$S: 335.1042; Found: 335.1041.

Preparation of Compound (15)

Neat compound (14) (1.0 g, 2.99 mmol) was stirred and heated under argon at 238–243° C. in an oil bath for 9 hours. The complete reaction was observed by thin layer chromatography (TLC) (silica gel, ethyl acetate/hexane 3/7) by the disappearance of (14) and a new spot displayed at TLC which is more polar than (14). The reaction was allowed to cool to room temperature. The oily residue was purified by flash column chromatography (silica gel) using ethyl acetate/hexane=3/7 as an eluent to give (15) (0.702 g, 70% yield). $^1$H-NMR (CDCl$_3$, 400 MHz) δ: 7.35–7.27 (m, 3H), 7.13 (m, 1H), 6.75 (m, 1H, NH), 4.22 (m, 1H), 3.07 (s, 3H), 2.98 (s, 3H), 2.80–2.72 (m, 2H), 1.11 (d, J=6.7 Hz, 3H); $^{13}$C-NMR (CDCl$_3$, 100 MHz) δ: 167.35, 156.8, 138.11, 137.16, 134.40, 130.67, 129.41, 128.92, 47.49, 41.56, 37.33, 19.57; HRFAB-MS Calcd for C$_{14}$H$_{18}$F$_3$N$_2$O$_2$S: 335.1042; Found: 335.1041.

Preparation of Compound (16)

To a stirred solution of (15) (678 mg, 2.01 mmol) in THF (60 ml) under argon was added KH (231 mg, 5.75 mmol, freed from protective mineral oil by washing with hexane three times followed by centrifugation). The reaction mixture was stirred for 10 minutes and 18-crown-6 (230 mg) and MeI (2.0 mL, 32 mmol) was added to the mixture. The reaction mixture was allowed to stir at room temperature for 2 hours and refluxed for 16 hours. Most of THF was removed by rotary evaporation and ethyl acetate (60 ml) was added to the mixture followed by cautiously adding of 10% aqueous HCl (10 ml) and water (20 ml). The organic phase was separated and the aqueous phase was extracted with ethyl acetate (3×50 ml) and the combined organic phase were washed with water (30 ml) and dried over $MgSO_4$. The organic solvent was filtered and evaporated to dryness by rotary evaporation. The residue was purified by flash column chromatography (silica gel) using ethyl acetate/hexane (3/7) as an eluent to give (16) (490 mg, 72% yield). $^1$H-NMR ($CDCl_3$, 400 MHz) δ: 7.36–7.19 (m, 4H), 4.75, 4.20 (m, 1H), 3.08 (s, 3H), 2.98 (s, 3H), 2.90, 2.93 (s, 3H), 2.87–2.75 (m, 2H), 1.22 (m, 3H); $^{13}$C-NMR ($CDCl_3$, 100 MHz) δ: 167.20, 157.12, 138.60, 138.20, 136.65, 134.65, 134.41, 130.12, 129.63, 124.19, 54.58, 53.12, 41.17, 39.54, 37.33, 29.81, 28.46, 18.30, 16.98; HRFAB-MS Calcd for $C_{15}H_{20}F_3N_2O_2S$: 349.1198; Found: 349.1194.

Preparation of Compound (17)

A mixture of (16) (457 mg, 1.31 mmol) and KOH (1.1 g, 19.6 mmol) in EtOH (24 ml) and water (16 ml) was refluxed under argon for 6 hours. The reaction mixture was allowed to cool to room temperature. The aqueous solution was acidified with 1N HCl (pH about 3). Most of ethanol was evaporated by rotary evaporation. The aqueous phase was frozen in dry ice and lyophilized to give hydrochloride salt of (17). $^1$H-NMR ($D_2O$, 400 MHz) δ: 7.40–7.00 (m, 4H), 3.40 (m, 1H), 2.93 (m, 1H), 2.72 (m, 1H), 2.62 (s, 3H), 1.17 (d, J=6.5 Hz, 3H).

Preparation of Compound (18)

To a stirred solution of (17) in THF (18 ml) and water (6 ml) was added di-tert-butyl-dicarbonate (571 mg, 2.62 mmol) and $K_2CO_3$ (387 mg, 2.80 mmol) at 0° C. The reaction mixture was stirred at room temperature for 2 hours under argon. Water (15 ml) was added to the mixture and most of THF was evaporated by rotary evaporation. The aqueous phase was extracted with ethyl acetate (3×70 ml) and the combined organic phase was washed with saturated NaCl solution (35 ml) and dried over $MgSO_4$. The organic solvent was filtered and evaporated to dryness. The residue was purified by flash column chromatography (silica gel) using ethyl acetate/hexane (15/85) as an eluent to give (18) (295 mg, 84.2%) and its disulfide dimer (18a) (40 mg, 11.4%). (18): FAB-MS:(MH$^+$, 282); $^1$H-NMR ($CDCl_3$, 400 MHz) δ: 7.20–6.80 (m, 4H), 4.46–4.32 (m, 1H), 3.39 (s, 1H, SH), 2.73–2.50 (m, 5H), 1.37–1.30 (m, 9H) 1.12 (m, 3H); $^{13}$C-NMR ($CDCl_3$, 100 MHz) δ: 155.87, 147.14, 140.45, 133.03, 130.93, 130.30, 129.37 127.67, 126.83, 85.59, 79.61, 52.81, 51.44, 40.77, 28.75, 28.59, 27.82, 18.89, 17.96.

Preparation of Compound (19)

To a stirred solution of (11) (87 mg, 0.216 mmol) in acetone (15 ml) was added a solution of (18) (61 mg, 0.217 mmol) in acetone (1 ml) and diisopropylethyl amine (45 uL, 0.258 mmol). The reaction mixture was stirred at room temperature for 45 minutes. The complete reaction was observed by the disappearance of compound (11) on TLC. Acetone was evaporated to dryness. The residue was purified by flash column chromatography (silica gel) using ethyl acetate/hexane (2/3) as an eluent to give compound (19) (110 mg, 84%). EI-MS m/z: 602 (M$^+$, 18), 502 (62), 158 (56), 102 (100); $^1$H-NMR ($CDCl_3$, 400 MHz) δ: 7.25–7.00 (m, 8H), 4.42–4.26 (m, 2H), 3.82(m, 4H), 2.78–2.55 (m, 8H), 1.41–1.24 (m, 18H), 1.11–1.02(m, 6H); FAB-HRMS Calculated (Calcd) for $C_{32}H_{46}N_2O_5S_2Li$ (MLi$^+$): 609.3011; Found: 609.3008.

Preparation of Compound (20)

To a stirred solution of (19) (80 mg, 0.1327 mmol) (obtained as described above) in MeOH (15 ml) was added ammonium acetate (194 mg, 2.51 mmol). The reaction mixture was stirred at room temperature for 2 hours. Sodium cyanoborohydride (43 mg, 0.65 mmol) was added into the mixture. The reaction mixture was stirred at room temperature for 16 hours. The complete reaction was observed by the disappearance of compound (19) on TLC and a more polar spot displayed (silica gel, ethyl acetate/hexane=2/3). Acetic acid (0.14 mL) was added to the reaction. The MeOH were evaporated to dryness by rotary evaporation. The residue was purified by flash column chromatography (silica gel) using MeOH/$CH_2Cl_2$ (1/9) as an eluent to give (20) (69 mg, 86% yield). EI-MS m/z: 604 (M$^+$, 51), 323 (76), 309 (45), 102 (100); $^1$H-NMR ($CDCl_3$, 400 MHz) δ: 7.25–6.96 (m, 8H), 4.45–4.43 (m, 4H), 3.19(m, 5H), 2.67 (m, 8H), 1.42–1.20 (m, 18H), 1.13–1.05 (m, 6H); EI-HRMS Calcd for $C_{32}H_{49}N_3O_4S_2$(M$^+$): 603.3164; Found: 603.3177.

Preparation of Compound (21)

To a stirred solution of (20) (22 mg, 0.0364 mmol) (obtained as described above) in THF (4 ml) was added diisopropylethylamine (50 μL, 0.286 mmol) and bromoacetic acid N-hydroxy succinimide (30 mg, 0.127 mmol) at 0° C. under argon. The reaction mixture was stirred at room temperature for 1.5 hours. Water (5 ml) was added and most of the THF was removed by rotary evaporation. The aqueous phase was extracted with $CH_2Cl_2$ (3×30 ml). The combined organic phase were washed with water (15 mL) and dried over $MgSO_4$. The combined organic phase was filtered and evaporated to dryness by rotary evaporation. The residue was purified by flash column chromatography (silica gel) using ethyl acetate/hexane (2/3) as an eluent to give (21) (19 mg, 72% yield.) FAB-MS: (MLi$^+$, Br$^{79}$): 730; (MLi$^+$, Br$^{81}$) 732; Found: 730 (Br$^{79}$); 732 (Br$^{81}$); $^1$H-NMR ($CDCl_3$, 400 MHz) δ: 7.22–7.00 (m, 8H), 4.65–4.20 (m, 3H), 3.90 (m, 1H), 3.68 (d, J=5.1 Hz, 2H), 3.34–3.30 (m, 2H), 3.19–3.15 (m, 2H), 2.85–2.61 (m, 8H), 1.41–1.26 (m, 18H), 1.12–1.05 (m, 6H); FAB-HRMS Calcd for $C_{34}H_{50}BrN_3O_5S_2Li$ (MLi$^+$, Br$^{79}$): 730.2535; (MLi$^+$, Br$^{81}$): 732.2515; Found: 730.2540 (Br$^{79}$), 732.2543 (Br$^{81}$).

Preparation of Compound (22)

To a solution of (21) (18 mg, 0.0248 mmol) (obtained as described above) in $CH_2Cl_2$ (2 ml) was added trifluoroacetic acid (0.4 ml, 5.23 mmol). The reaction was stirred at room temperature for 40 minutes. The excess of trifluoroacetic acid and the solvent $CH_2Cl_2$ were removed by rotary evaporation and put in high vacuum. This gave the desired product (22) (18 mg, 96% yield). FAB-MS: (MH$^+$, Br$^{79}$): 524; (MH$^+$, Br$^{81}$) 526; Found: 524 (Br$^{79}$), 526 (Br$^{81}$); FAB-HRMS Calcd for $C_{24}H_{35}BrN_3OS_2$ (MH$^+$, Br$^{79}$): 524.1404, (MH$^+$, Br$^{81}$): 526.1384; Found: 524.1400 (Br$^{79}$), 526.1394 (Br$^{81}$).

Preparation of Compound (23)

To a stirred solution of (20) (23 mg, 0.38 mmol) in THF (4 ml) was added diisopropylethylamine (50 μL, 0.286 mmol) and bromoacetylglycine N-hydroxy succinimide (36 mg, 0.123 mmol) at 0° C. under argon. The reaction mixture was stirred at room temperature for 3 hours. Water (5 ml) was added and most of the THF was removed by rotary evaporation. The aqueous phase was extracted with $CH_2Cl_2$ (3×30 ml). The combined organic phase were washed with water (15 ml) and dried over $MgSO_4$. The combined organic phase was filtered and concentrated to dryness by rotary evaporation. The residue was purified by flash column chromatography (silica gel) using ethyl acetate/hexane (3/2) as an eluent to give (23) (6 mg, 20.2% yield). FAB-MS: ($MLi^+$, $Br^{79}$): 787; ($MLi^+$, $Br^{81}$) 789; Found: 787 ($Br^{79}$), 789 ($Br^{81}$); FAB-HRMS Calcd for $C_{36}H_{53}BrN_4O_6S_2Li$ ($MLi^+$, $Br^{79}$): 787.2749, ($MLi^+$, $Br^{81}$): 789.2729; Found: 787.2776 ($Br^{79}$), 789.2774 ($Br^{81}$).

Preparation of Compound (24)

To a solution of (23) (4 mg, 0.00512 mmol) (obtained as described above) in $CH_2Cl_2$ (2 mL) was added trifluoroacetic acid (0.3 mL, 3.92 mmol). The reaction was stirred at room temperature for 60 minutes. The excess of trifluoroacetic acid and the solvent $CH_2Cl_2$ were removed by rotary evaporation and further dried under high vacuum. This gave the desired product 24 (4 mg, 96% yield). FAB-MS: ($MH^+$, $Br^{79}$): 581; ($MH^+$, $Br^{81}$) 583; Found: 581 ($Br^{79}$), 583 ($Br^{81}$); FAB-HRMS Calcd for $C_{26}H_{38}BrN_4O_2S_2$ ($MH^+$, $Br^{79}$): 581.1619, ($MH^+$, $Br^{81}$): 583.1599; Found: 581.1612 ($Br^{79}$), 583.1582 ($Br^{81}$).

Preparation of Enzyme Conjugates Using Bivalent Haptens (22) and (24)

Bivalent haptens (22) and (24), prepared as described above, were allowed to react with a glucose-6-phosphate dehydrogenase (G6PDH) mutant enzyme to form the bivalent hapten/enzyme conjugate. In this mutant enzyme, one amino acid in the primary amino acid sequence has been replaced with a cysteine. The mutant enzyme was obtained by the procedure disclosed in U.S. Pat. Nos. 6,090,567 and 6,033,890, the relevant disclosures of which were incorporated hereinabove by reference. The conjugation technique disclosed in U.S. Pat. Nos. 6,090,567 and 6,033,890 was then utilized to couple the bivalent hapten to the enzyme through a thioether linkage. The preparation is described in U.S. Pat. No. 6,090,567 in particular at column 28, line 44, to column 43, line 29, the disclosure of which is incorporated herein by reference.

Inhibition of the Bivalent Hapten/G6PDH Conjugates by Amphetamine and Methamphetamine Antibodies.

For a conjugate to have utility in EMIT assays, the antibody must inhibit the conjugate. Therefore, conjugates prepared with bivalent haptens (22) and (24) (as described above) were incubated in the presence of amphetamine and methamphetamine antibodies and tested for activity. The conditions and duration of incubation were as follows: An appropriate dilution of conjugate prepared with bivalent hapten (22) or (24) was mixed with either amphetamine or methamphetamine antibody, deionized water and glucose-6-phosphate dehydrogenase substrates, at an appropriate pH and ionic strength, in a final volume of 318 μL. After a 100-second incubation at 37° C., the enzyme activity (ΔA/min at 340 nm) was measured. Control experiments with deionized water instead of antibody established the uninhibited baseline activity, which was compared to the activity in the presence of antibody to establish the degree of antibody dependent conjugate inhibition. The results shown in FIG. 1 demonstrate that when the enzyme conjugate prepared with bivalent hapten (24) was allowed to interact with either amphetamine or methamphetamine antibody, there was an antibody concentration dependent inhibition of the conjugate. Antibody concentration dependent inhibition of enzyme conjugate prepared with bivalent hapten (22) was also observed (results not shown). Enzyme conjugate prepared with bivalent hapten (24) was selected for further testing.

Utilization of the Enzyme Conjugate of Bivalent Hapten (24) to Generate Individual Standard Curves with Amphetamine or Methamphetamine In order to test the presentation of the bivalent hapten (24) in the enzyme conjugate to the antibody, competition experiments were performed between the enzyme conjugate and either amphetamine or methamphetamine and the corresponding antibody. The conditions and duration of incubation were as follows:

Methamphetamine calibrator solutions were prepared by diluting a stock solution of methamphetamine (2000 ng/mL in urine) with methamphetamine negative urine, to final concentrations of 1000 ng/mL, 600 ng/mL, 400 ng/mL, 200 ng/mL and 100 ng/mL. Amphetamine calibrator solutions were prepared by diluting a stock solution of amphetamine (2000 ng/mL in urine) with amphetamine negative urine, to final concentrations of 1000 ng/mL, 600 ng/mL, 400 ng/mL, 200 ng/mL and 100 ng/mL. In order to generate the standard curve for amphetamine with amphetamine antibody, an appropriate volume of each amphetamine calibrator was incubated with an appropriate dilution of amphetamine antibody for 300 sec at 37° C. Conjugate prepared with bivalent hapten (24) was then added and after an additional incubation of 100 sec, the enzyme activity (ΔA/min at 340 nm) was determined. Enzyme activities were normalized by subtracting the enzyme activity observed when negative (0 ng/mL) calibrator was used as the sample, from the enzyme activity observed when each calibrator solution was used as the sample. Results were then plotted as enzyme activity in normalized units versus the concentration of amphetamine calibrator used. The standard curve for methamphetamine calibrators with methamphetamine antibody was generated in an analogous manner as that for amphetamine.

Figure 3:
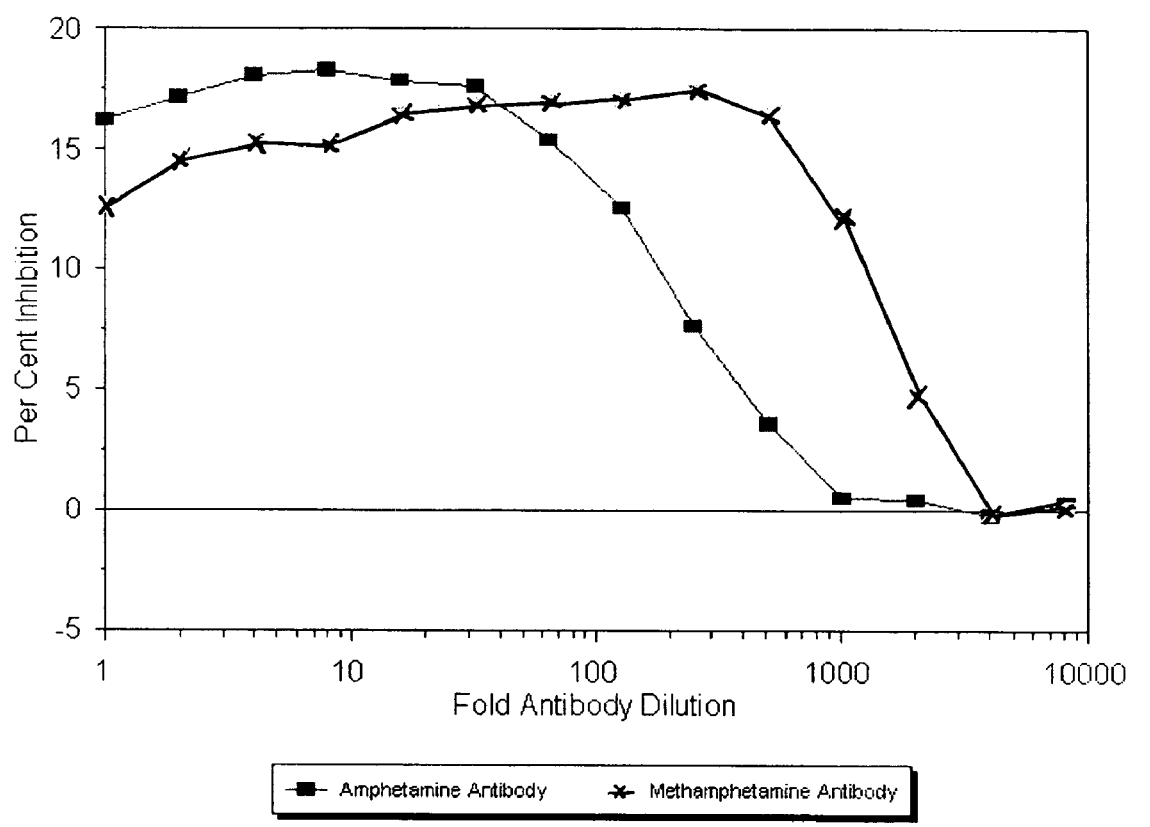
FIG. 3 is a graph depicting the inhibition of enzyme bivalent hapten conjugate by amphetamine and methamphetamine antibodies.

FIG. 2 shows the standard curve for amphetamine with amphetamine antibody. FIG. 3 shows the standard curve for methamphetamine and methamphetamine antibody. A drug concentration dependent response can be seen clearly when the enzyme conjugate of bivalent hapten (24) was tested with either the amphetamine and corresponding antibody or the methamphetamine and corresponding antibody.

Assay for Amphetamine and Methamphetamine

Figure 4:
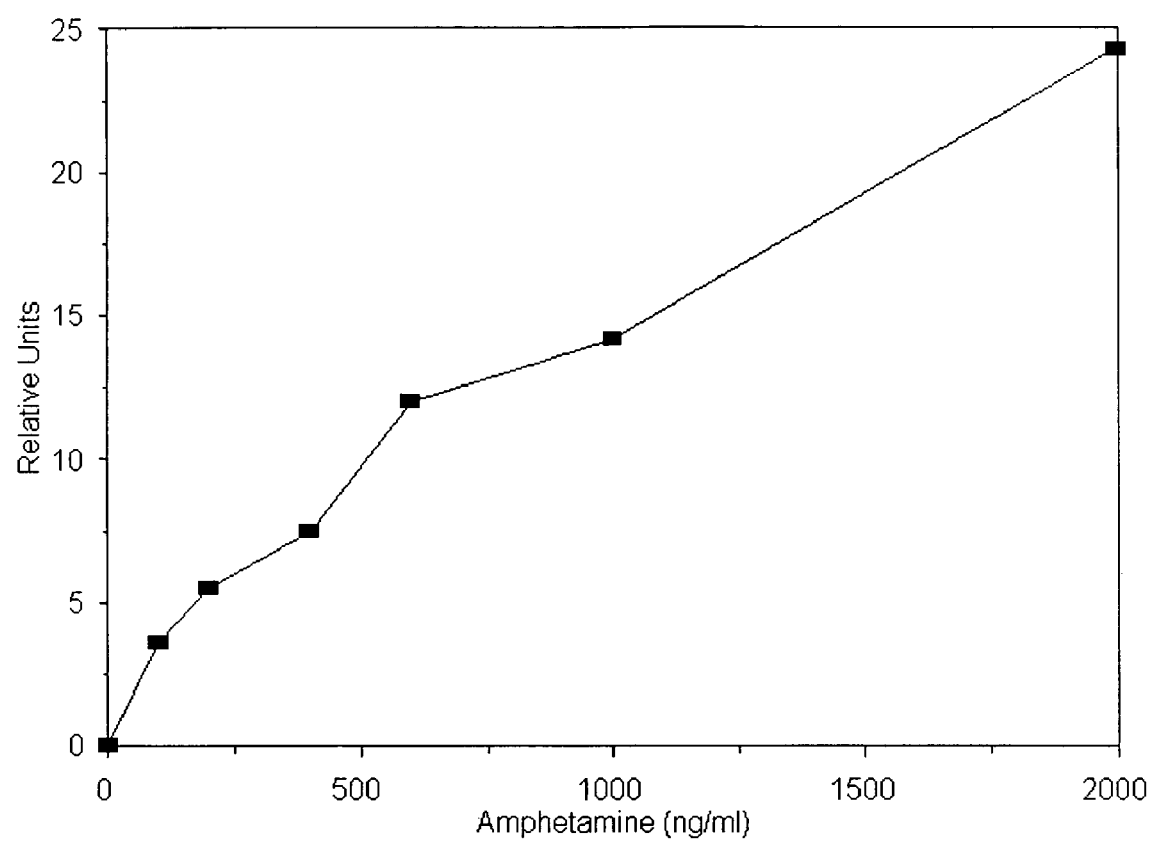
FIG. 4 is a graph depicting a standard curve for amphetamine with an enzyme bivalent hapten conjugate in accordance with the present invention.
Figure 5:
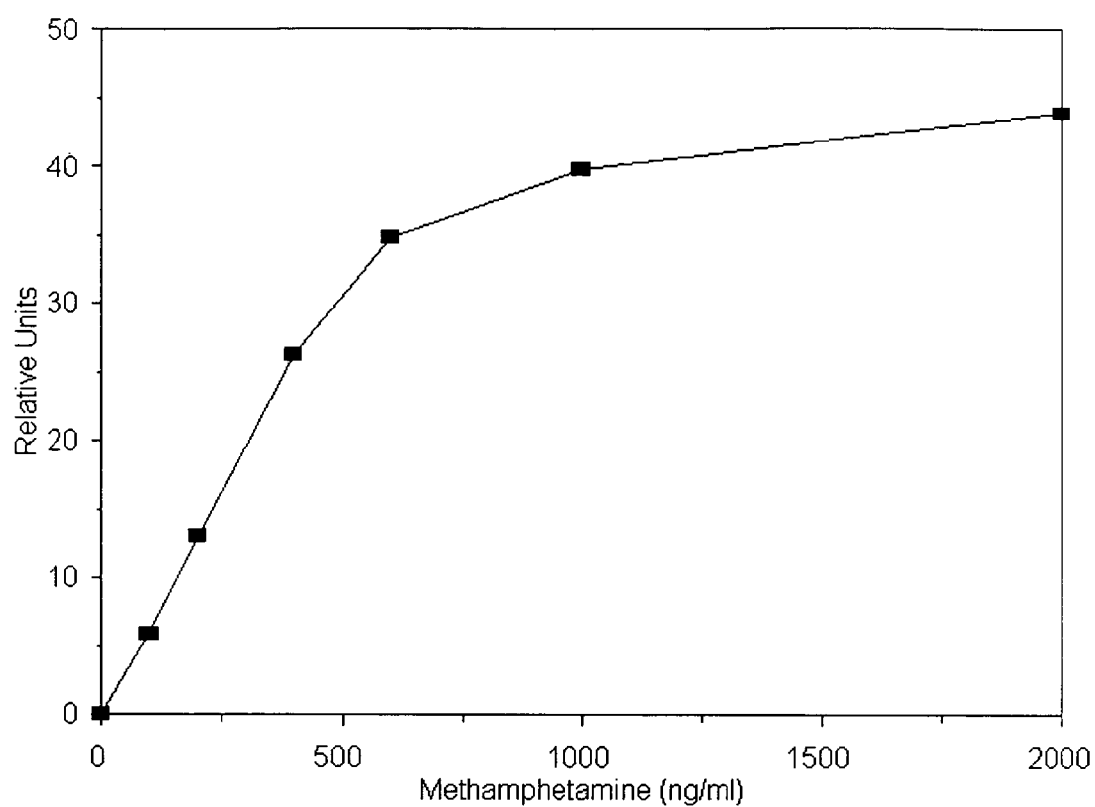
FIG. 5 is a graph depicting a standard curve for detection of methamphetamine with an enzyme bivalent hapten conjugate in accordance with the present invention.
Figure 6:
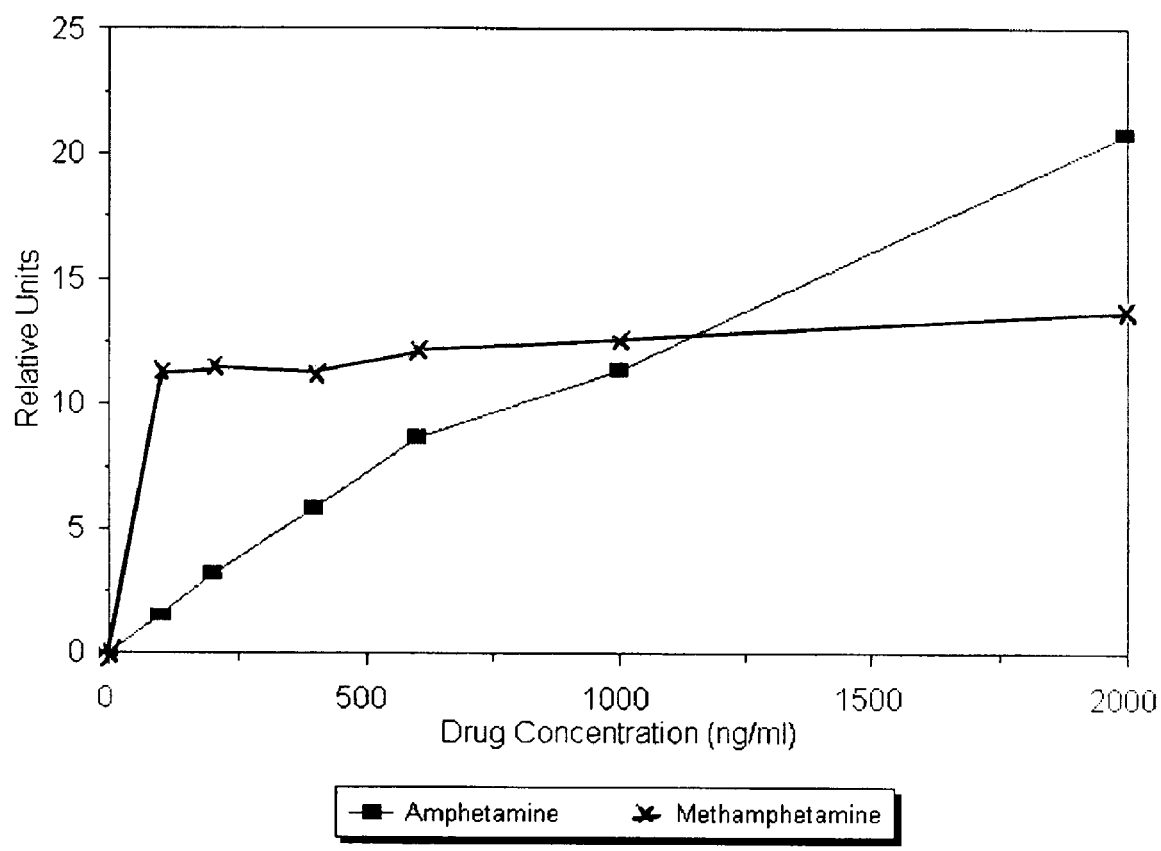
FIG. 6 is a graph depicting results of the detection of amphetamine and methamphetamine in a three-component system

The enzyme conjugate of bivalent hapten (24) in conjunction with a mixture of amphetamine and methamphetamine antibodies was employed to detect the presence of either amphetamine or methamphetamine in a sample. The conditions and duration of incubation were as follows:

Methamphetamine calibrator solutions were prepared by diluting a stock solution of methamphetamine (2000 ng/mL in urine) with methamphetamine negative urine, to final concentrations of 1000 ng/mL, 600 ng/mL, 400 ng/mL, 200 ng/mL and 100 ng/mL. Amphetamine calibrator solutions were prepared by diluting a stock solution of amphetamine (2000 ng/mL in urine) with amphetamine negative urine, to final concentrations of 1000 ng/mL, 600 ng/mL, 400 ng/mL, 200 ng/mL and 100 ng/mL. An antibody reagent consisting of methamphetamine antibody plus amphetamine antibody mixed in an appropriate ratio was prepared. In order to generate the standard curve for amphetamine with the amphetamine plus methamphetamine antibody reagent, an appropriate volume of each amphetamine calibrator was incubated with an appropriate dilution of the antibody reagent for 300 sec at 37° C. Conjugate prepared with bivalent hapten (24) was then added and after an additional incubation of 100 sec, the enzyme activity (ΔA/min at 340 nm) was determined. Enzyme activities were normalized by subtracting the enzyme activity observed when negative (0 ng/mL) calibrator was used as the sample, from the enzyme activity observed when each calibrator solution was used as the sample. Methamphetamine calibrators were then tested with the amphetamine plus methamphetamine antibody reagent in an analogous manner. Results were then plotted as enzyme activity in normalized units versus the concentration of amphetamine or methamphetamine calibrator used. FIG. 4 shows that a combination of the enzyme conjugate and both amphetamine and methamphetamine antibodies detected the presence of either amphetamine or methamphetamine in a sample.

The above discussion includes certain theories as to mechanisms involved in the present invention. These theories should not be construed to limit the present invention in any way, since it has been demonstrated that the present invention achieves the results described.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A compound comprising an amphetamine moiety and a methamphetamine moiety linked together by a first linking group wherein a second linking group is linked to said first linking group and the distance of the amphetamine moiety and the methamphetamine moiety from the point of linkage of said second linking group to said first linking group is approximately the same and wherein said second linking group terminates in a functional group.

2. A compound according to claim 1 further comprising a poly(amino acid) or a non-poly(amino acid) label moiety linked to said second linking group by means of said functional group.

3. A compound according to claim 1 wherein said distance is equal.

4. A compound according to claim 1 wherein said amphetamine and said methamphetamine are stereospecific.

5. A compound of the formula:

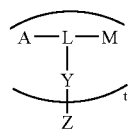

wherein:
A is an amphetamine moiety,
M is a methamphetamine moiety,
L is a linking group,
Y is a bond or a linking group and is bonded to L at a point equidistant between A and M, and
Z is a poly(amino acid), a non-poly(amino acid) label moiety or a functional group;
t is 1 when Z is a functional group or a non-poly(amino acid) label or, when Z is a poly(amino acid), t is an integer between 1 and the molecular weight of a poly(amino acid) divided by about 500;
and salts thereof.

6. A compound according to claim 5 wherein A and M are linked to L from the same corresponding positions in A and M.

7. A compound according to claim 5 wherein Z is an enzyme label.

8. A compound according to claim 5 wherein said amphetamine moiety and said methamphetamine moiety are stereospecific.

9. A compound according to claim 5 wherein A is:

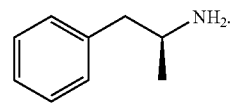

10. A compound according to claim 5 wherein M is:

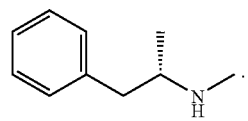

11. A compound of the formula:

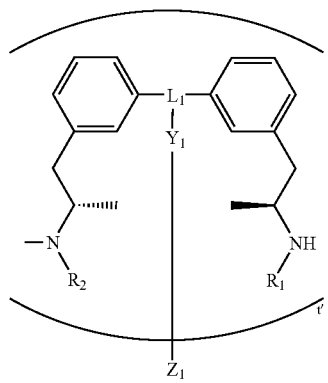

wherein:
$R_1$ is hydrogen, lower alkyl or a protecting group, $R_2$ is hydrogen, lower alkyl or a protecting group,
$L_1$ is a linking group,
$Y_1$ is a bond, a functional group or a linking group and is bonded to $L_1$ at a point equidistant between the point of attachment to each of the phenyl groups,
$Z_1$ is a poly(amino acid), a non-poly(amino acid) label or a functional group; and
t' is 1 when $Z_1$ is a functional group or a non-poly(amino acid) label or, when $Z_1$ is a poly(amino acid), t' is an integer between 1 and the molecular weight of a poly(amino acid) divided by about 500;
and salts thereof.

12. A compound according to claim 11 wherein $Z_1$ is an enzyme label.

13. A compound according to claim 11 wherein $R_1$ is hydrogen.

14. A compound according to claim 11 wherein $R_2$ is methyl.

15. A compound of the formula:

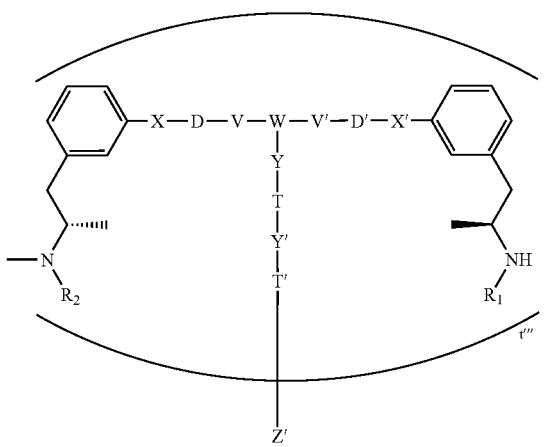

wherein:
$R_1$ and $R_2$ are independently H or a protecting group,
X and X' are independently O, S, or a bond;
D and D' are independently alkylene or substituted alkylene;
V and V' are independently O, S, or a bond;
W is CH;
Y is $NR_3$ wherein $R_3$ is H or lower alkyl, O, S, or a bond;
T is alkylene, —(C=O)alkylene, ethereal alkylene, acetamide or a bond;
Y' is $NR_3$ wherein $R_3$ is H or lower alkyl, O, S, or a bond;
T' is alkylene, —(C=O)alkylene, ethereal alkylene, acetamide or a bond; and
Z' is a poly(amino acid), a non-poly(amino acid) label moiety, H, Br, Cl, F, I, $NH_2$, acetamide, or haloacetamide;
t" is 1 when Z' is a functional group or a non-poly(amino acid) label or, when Z' is a poly(amino acid), t" is an integer between 1 and the molecular weight of a poly(amino acid) divided by about 500;
with the proviso that X and X' have approximately the same length, D and D' have approximately the same length, and V and V' have approximately the same length;
and salts thereof.

16. A compound according to claim 15 wherein Z' is an enzyme label.

17. A compound according to claim 15 wherein X and X' are S.

18. A compound according to claim 15 wherein D and D' are methylene.

19. A compound according to claim 15 wherein Y and Y' are NH.

20. A compound according to claim 15 wherein T and T' are —(C=O)$CH_2$—.

21. A compound of the formula:

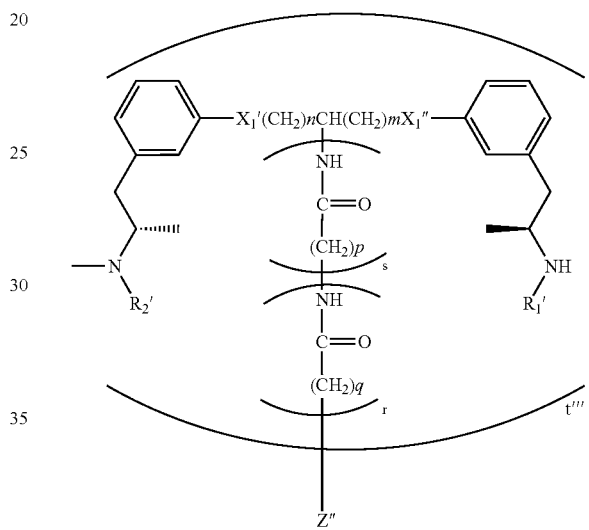

wherein:
$R_1$' and $R_2$' are independently H or a protecting group,
$X_1$' and $X_1$" are S or O;
Z" is an enzyme; H, Br, Cl, F, I, $NH_2$, acetamide, or haloacetamide;
t''' is 1 when Z" is other than an enzyme label and, when Z" is an enzyme label, t''' is an integer between 1 and the molecular weight of said enzyme label divided by about 500; and
n, m, p, q are each independently 1 to 5 and r and s are each independently 0 to 5;
and salts thereof.

22. A compound according to claim 21 wherein $R_1$' and $R_2$' are H, $X_1$' and $X_1$" are S, n, m, p, q, r and s are 1, and Z" is an enzyme label.

23. A compound according to claim 21 wherein $R_1$' and $R_2$' are H or a protecting group, $X_1$' and $X_1$" are S, n and m are 1, r and s are 0, and Z" is $NH_2$.

24. A compound according to claim 21 wherein $R_1$' and $R_2$' are H or a protecting group, $X_1$' and $X_1$" are S, n and m are 1, r is 1 and s is 0, and Z" is Br.

25. A compound according to claim 21 wherein $R_1$' and $R_2$' are H or a protecting group, $X_1$' and $X_1$" are S, n and m are 1, r and s are 1, and Z" is Br.

26. A compound of the formula:

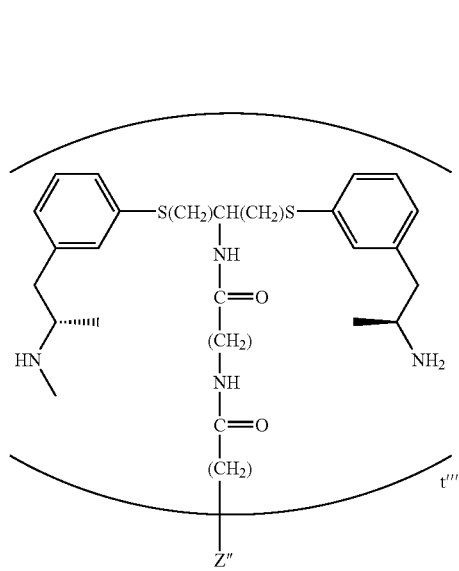

wherein:

Z" is an enzyme label; and t"' is an integer between 1 and the molecular weight of said enzyme label divided by about 500.

27. A compound according to claim 26 wherein said enzyme label is glucose-6-phosphate dehydrogenase.

28. A reagent system comprising a compound according to claim 26, an antibody for amphetamine and an antibody for methamphetamine.

29. A method for determining amphetamine and/or methamphetamine in a sample suspected of containing amphetamine and/or methamphetamine, said method comprising:

(a) providing in combination in a medium:

(i) said sample and (ii) a reagent system according to claim 28; and (b) examining for the presence or amount of signal from said enzyme, the presence or amount thereof indicating the presence or amount of said amphetamine and/or methamphetamine in said sample.

30. A method according to claim 29 wherein said method is a homogeneous method.

31. A method according to claim 29 wherein said method is a heterogeneous method.

32. A method far determining amphetamine and/or methamphetamine in a sample suspected of containing amphetamine and/or methamphetamine, said method comprising:

(a) providing in combination in a medium:

(i) said sample, (ii) an antibody for amphetamine, (iii) an antibody for methamphetamine, (iv) a compound of the formula:

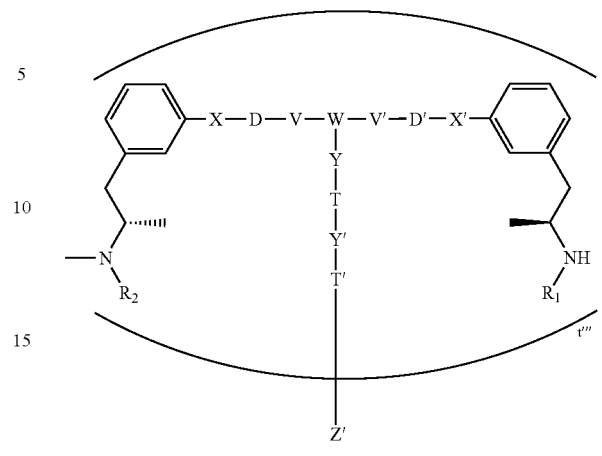

wherein:

$R_1$ and $R_2$ are H,

X and X' are independently O, S, or a bond;

D and D' are independently alkylene or substituted alkylene;

V and V' are independently O, S, or a bond;

W is CH;

Y is O, S, a bond, or $NR_3$ wherein $R_3$ is H or lower alkyl;

T is alkylene, —(C═O)alkylene, ethereal alkylene, acetamide or a bond;

Y' is O, S, a bond, or $NR_3$ wherein $R_3$ is H or lower alkyl;

Y' is alkylene, —(C═O)alkylene, ethereal alkylene, acetamide or a bond; and

Z' is an enzyme;

t" is an integer between 1 and the molecular weight of said enzyme divided by about 500; with the proviso that X and X' have approximately the same length, D and D' have approximately the same length, and V and V' have approximately the same length; and (b) examining for the presence or amount of signal from said enzyme, the presence or amount thereof indicating the presence or amount of said amphetamine and/or methamphetamine in said sample.

33. A method according to claim 32 wherein said method is a homogeneous method.

34. A method according to claim 32 wherein said method is a heterogeneous method.

35. A method according to claim 32 wherein said enzyme is glucose-6-phosphate dehydrogenase.

36. A method for determining amphetamine and/or methamphetamine in a sample suspected of containing amphetamine and/or methamphetamine, said method comprising:

(a) providing in combination in a medium:

(i) said sample, (ii) an antibody for amphetamine, (iii) an antibody for methamphetamine, (iv) a compound of the formula:

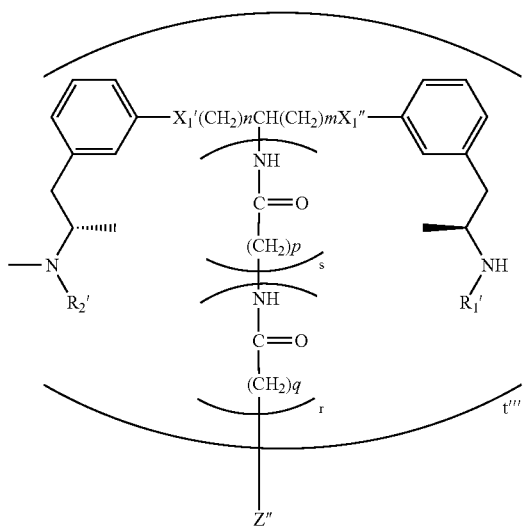

wherein:
R$_1$' and R$_2$' are H,
X$_1$' and X$_1$" are S or O;
Z" is an enzyme;
t'" is an integer between 1 and the molecular weight of said enzyme divided by about 500; and
n, m, p, q, r and s are each independently 1 to 5; and
(b) examining for the presence or amount of signal from said enzyme, the presence or amount thereof indicating the presence or amount of said amphetamine and/or methamphetamine in said sample.

37. A method according to claim 36 wherein said method is a homogeneous method.

38. A method according to claim 36 wherein said method is a heterogeneous method.

39. A method according to claim 36 wherein said enzyme is glucose-6-phosphate dehydrogenase.

40. A kit comprising in packaged combination:
(i) an antibody for amphetamine,
(ii) an antibody for methamphetamine,
(iii) a compound of the formula:

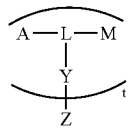

wherein:
A is an amphetamine moiety,
M is a methamphetamine moiety,
L is a linking group,
Y is a bond or a linking group and is bonded to L at a point equidistant between A and M,
Z is an enzyme,
t is an integer between 1 and the molecular weight of said enzyme divided by about 500.

41. A kit according to claim 40 wherein A and M are linked to L from the same corresponding position in A and M.

42. A kit according to claim 40 wherein said amphetamine and said methamphetamine are stereospecific.

43. A kit according to claim 40 wherein said enzyme is glucose-6-phosphate dehydrogenase.

44. A kit according to claim 40 wherein said compound has the formula:

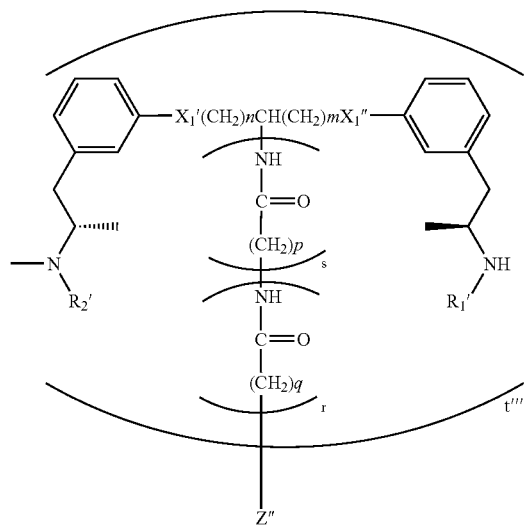

wherein:
R$_1$' and R$_2$' are H,
X$_1$' and X$_1$" are S or O;
Z" is an enzyme;
t'" is an integer between 1 and the molecular weight of said enzyme divided by about 500; and
n, m, p, q, r and s are each independently 1 to 5.

* * * * *

UNITED STATES PATENT AND TRADEMARK OFFICE
CERTIFICATE OF CORRECTION

PATENT NO. : 7,115,383 B2  Page 1 of 1
APPLICATION NO. : 10/806327
DATED : October 3, 2006
INVENTOR(S) : Zheng et al.

It is certified that error appears in the above-identified patent and that said Letters Patent is hereby corrected as shown below:

1) In Claim 32, Col. 37, line 58, please delete "far" and insert --for--.
2) In Claim 32, Col. 38, line 37, please delete "Y" and insert --T'-- in front of "is alkylene".

Signed and Sealed this

Sixth Day of March, 2007

JON W. DUDAS
*Director of the United States Patent and Trademark Office*